United States Patent
Demmer et al.

(10) Patent No.: US 12,251,567 B2
(45) Date of Patent: Mar. 18, 2025

(54) PACING MODE SWITCHING AND RATE RESPONSE LIMIT IN A VENTRICULAR PACEMAKER

(71) Applicant: Medtronic, Inc., Minneapolis, MN (US)

(72) Inventors: Wade M. Demmer, Coon Rapids, MN (US); Juliana E. Pronovici, New Hope, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 17/531,699

(22) Filed: Nov. 19, 2021

(65) Prior Publication Data
US 2022/0096837 A1 Mar. 31, 2022

Related U.S. Application Data

(63) Continuation of application No. 15/948,240, filed on Apr. 9, 2018, now Pat. No. 11,185,701.

(51) Int. Cl.
*A61N 1/36* (2006.01)
*A61B 5/00* (2006.01)
(Continued)

(52) U.S. Cl.
CPC ........ *A61N 1/3688* (2013.01); *A61B 5/02444* (2013.01); *A61B 5/026* (2013.01); *A61B 5/1107* (2013.01); *A61B 5/287* (2021.01); *A61B 5/349* (2021.01); *A61B 5/352* (2021.01); *A61B 5/686* (2013.01); *A61N 1/025* (2013.01); *A61N 1/0573* (2013.01); *A61N 1/36507* (2013.01); *A61N 1/36578* (2013.01); *A61N 1/36585* (2013.01); *A61N 1/36592* (2013.01); *A61N 1/3704* (2013.01); *A61N 1/37211* (2013.01); *A61N 1/3756* (2013.01); *A61B 5/1118* (2013.01); *A61N 1/36542* (2013.01); *A61N 1/3682* (2013.01); *A61N 1/37205* (2013.01); *A61N 1/37288* (2013.01)

(58) Field of Classification Search
CPC .............................. A61B 5/352; A61N 1/3688
See application file for complete search history.

(56) References Cited

U.S. PATENT DOCUMENTS 5,052,388 A 10/1991 Sivula et al.
5,480,412 A 1/1996 Mouchawar et al.
(Continued)

OTHER PUBLICATIONS

European Communication dated Feb. 7, 2023, corresponding to counterpart C00016295EP01, European Patent Application No. 19719026.7, 6 pages.
(Continued)

*Primary Examiner* — Michael J D'Abreu

(57) ABSTRACT

An intracardiac ventricular pacemaker having a motion sensor, a pulse generator and a control circuit coupled to the pulse generator and the motion sensor is configured to identify a ventricular systolic event, detect a ventricular passive filling event signal from the motion signal, and determine a time interval from the ventricular systolic event to the ventricular passive filling event. The pacemaker establishes a minimum pacing interval based on the time interval.

19 Claims, 10 Drawing Sheets

(51) Int. Cl.

| | | |
|---|---|---|
| *A61B 5/024* | (2006.01) | |
| *A61B 5/026* | (2006.01) | |
| *A61B 5/11* | (2006.01) | |
| *A61B 5/287* | (2021.01) | |
| *A61B 5/349* | (2021.01) | |
| *A61B 5/352* | (2021.01) | |
| *A61N 1/02* | (2006.01) | |
| *A61N 1/05* | (2006.01) | |
| *A61N 1/365* | (2006.01) | |
| *A61N 1/368* | (2006.01) | |
| *A61N 1/37* | (2006.01) | |
| *A61N 1/372* | (2006.01) | |
| *A61N 1/375* | (2006.01) | |

(56) References Cited

U.S. PATENT DOCUMENTS

| | | |
|---|---|---|
| 5,507,782 A | 4/1996 | Kieval et al. |
| 5,593,431 A | 1/1997 | Sheldon |
| 5,683,432 A | 11/1997 | Goedeke et al. |
| 5,720,769 A | 2/1998 | van Oort et al. |
| 5,792,195 A | 8/1998 | Carlson et al. |
| 6,044,297 A | 3/2000 | Sheldon et al. |
| 6,836,682 B2 | 12/2004 | Van Dam |
| 7,031,772 B2 | 4/2006 | Condie et al. |
| 7,711,422 B2 | 5/2010 | Dal Molin |
| 8,233,981 B2 | 7/2012 | Casset |
| 8,433,409 B2 | 4/2013 | Johnson et al. |
| 8,532,771 B2 * | 9/2013 | Daum .................. A61N 1/365 |
| | | 607/18 |
| 8,532,785 B1 | 9/2013 | Crutchfield et al. |
| 8,541,131 B2 | 9/2013 | Lund et al. |
| 8,923,963 B2 | 12/2014 | Bonner et al. |
| 8,996,109 B2 | 3/2015 | Karst et al. |
| 9,272,146 B2 | 3/2016 | Anselmi |
| 9,399,140 B2 | 7/2016 | Cho et al. |
| 9,775,982 B2 | 10/2017 | Grubac et al. |
| 9,814,887 B2 | 11/2017 | Nikolski et al. |
| 10,207,116 B2 | 2/2019 | Sheldon et al. |
| 10,328,270 B2 | 6/2019 | Demmer et al. |
| 10,449,366 B2 | 10/2019 | Splett et al. |
| 10,532,212 B2 | 1/2020 | Splett et al. |
| 2012/0095521 A1 | 4/2012 | Hintz |
| 2016/0023000 A1 | 1/2016 | Cho et al. |
| 2016/0067490 A1 | 3/2016 | Carney et al. |
| 2016/0114161 A1 | 4/2016 | Amblard et al. |
| 2017/0274213 A1 | 9/2017 | Ghosh et al. |
| 2018/0021582 A1 | 1/2018 | An et al. |
| 2018/0085588 A1 | 3/2018 | Splett et al. |
| 2018/0085589 A1 | 3/2018 | Splett et al. |
| 2018/0117337 A1 | 5/2018 | Demmer et al. |

OTHER PUBLICATIONS (PCT/US2019/026255) PCT Notification of Transmittal of the International Search Report and the Written Opinion of the International Searching Authority, Mailed Jul. 25, 2019, 14 pages.

Office Action Issued in Chinese Patent Application No. 201980024578.1, Mailed Date: Jan. 30, 2024, 20 Pages.

* cited by examiner

PACING MODE SWITCHING AND RATE RESPONSE LIMIT IN A VENTRICULAR PACEMAKER

REFERENCE TO RELATED APPLICATIONS

This application is a continuation of U.S. patent application Ser. No. 15/948,240, filed on Apr. 9, 2018, the contents of which is incorporated herein by reference in its entirety.

TECHNICAL FIELD

The disclosure relates to a ventricular pacemaker and associated method for switching between an atrial tracking ventricular pacing mode and a non-atrial tracking ventricular pacing mode and limiting the ventricular pacing rate based on a motion sensor signal.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a ventricular pacemaker and techniques for controlling the ventricular pacing mode by switching between an atrial tracking pacing mode and a non-atrial tracking pacing mode. The ventricular pacemaker may be an intracardiac pacemaker and may be configured to detect atrial systolic events from a motion signal produced by a motion sensor included in the intracardiac ventricular pacemaker. The ventricular pacemaker, operating according to the techniques disclosed herein, automatically switches between an atrial tracking pacing mode and a non-atrial tracking pacing mode according to mode-switching criteria in order to provide an appropriate ventricular pacing rate that supports the patient's metabolic need.

In one example, the disclosure provides an intracardiac ventricular pacemaker including a pulse generator, a motion sensor, and a control circuit. The pulse generator is configured to generate and deliver pacing pulses to a ventricle of a patient's heart via electrodes coupled to the pacemaker. The motion sensor is configured to produce a motion signal. The control circuit is coupled to the motion sensor and the pulse generator and is configured to identify a ventricular systolic event, detect a ventricular passive filling event signal from the motion signal, determine a time interval from the ventricular systolic event to the ventricular passive filling event and establish a minimum pacing interval based on the time interval. The control circuit is further configured to determine a sensor indicated pacing rate interval based on the motion signal, compare the sensor indicated pacing rate interval to the minimum pacing interval, and control the pulse generator to deliver a ventricular pacing pulse at the minimum pacing interval in response to the sensor indicated pacing rate interval being less than the minimum pacing interval.

In another example, the disclosure provides a method performed by an intracardiac ventricular pacemaker having a motion sensor configured to produce a motion signal. The method includes identifying a ventricular systolic event by a control circuit of the pacemaker, detecting a ventricular passive filling event signal from the motion signal by the control circuit, determining a time interval from the ventricular systolic event to the ventricular passive filling event, establishing a minimum pacing interval based on the time interval, determining a sensor indicated pacing rate interval based on the motion signal, comparing the sensor indicated pacing rate interval to the minimum pacing interval, and controlling a pulse generator to deliver a ventricular pacing pulse at the minimum pacing interval in response to the sensor indicated pacing rate interval being less than the minimum pacing interval.

In another example, the disclosure provides a non-transitory, computer-readable medium storing a set of instructions, which, when executed by a control circuit of an intracardiac ventricular pacemaker having a motion sensor configured to produce a motion signal, cause the pacemaker to identify a ventricular systolic event, detect a ventricular passive filling event signal from the motion signal, determine a time interval from the ventricular systolic event to the ventricular passive filling event, establish a minimum pacing interval based on the time interval, determine a sensor indicated pacing rate interval based on the motion signal, compare the sensor indicated pacing rate interval to the minimum pacing interval, and deliver a ventricular pacing pulse at the minimum pacing interval in response to the sensor indicated pacing rate interval being less than the minimum pacing interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
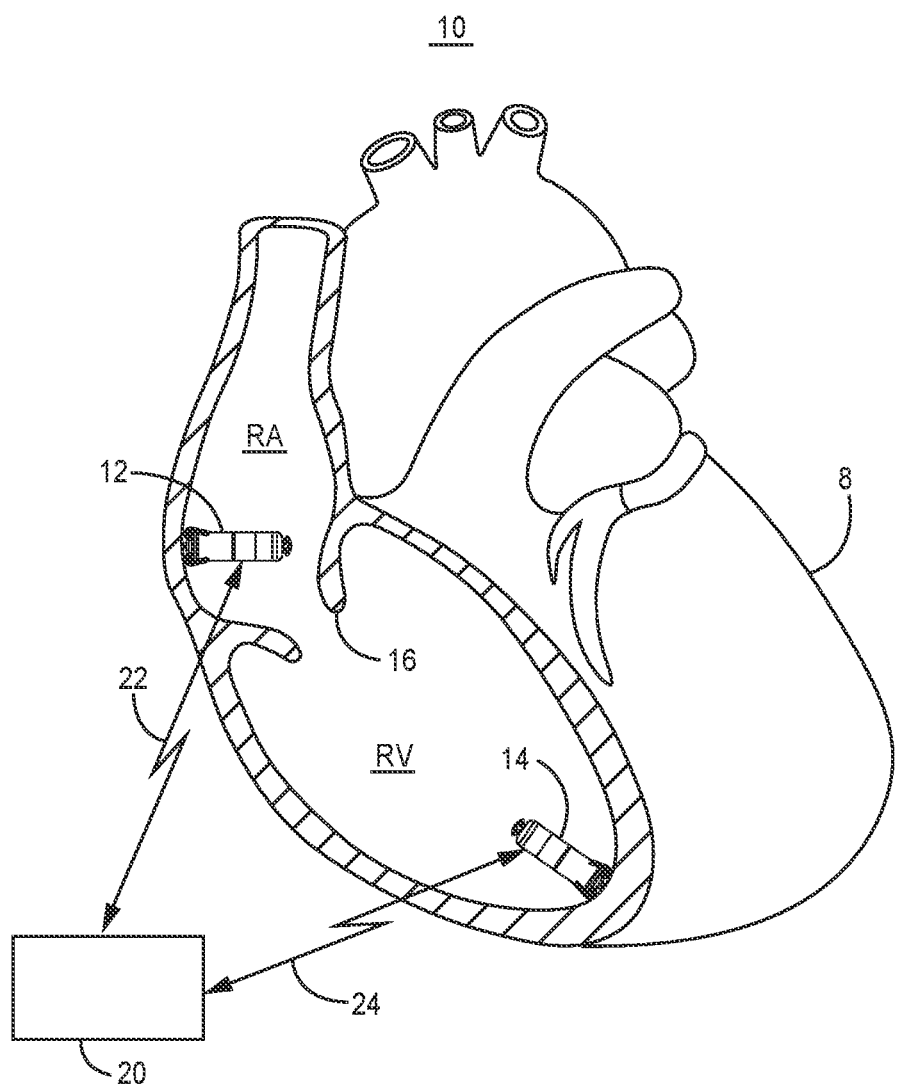
FIG. 1 is a conceptual diagram illustrating an intracardiac pacing system that may be used to sense cardiac electrical signals and motion signals induced by cardiac motion and flowing blood and provide pacing therapy to a patient's heart.

During atrial-synchronized ventricular pacing, ventricular pacing pulses are delivered at an atrioventricular (AV) pacing interval following an atrial event to provide proper synchrony between the atrial contraction and the ventricular contraction. In order for a ventricular intracardiac pacemaker to provide atrial-synchronized ventricular pacing, the ventricular intracardiac pacemaker needs to receive a signal indicating the timing of the atrial event in order to start the AV pacing interval. As the atrial rate increases or decreases, the ventricular pacing rate tracks the atrial rate. This atrial synchronized ventricular pacing is referred to as an "atrial-tracking" pacing mode. In a non-atrial tracking ventricular pacing mode, the ventricular pacing pulses are delivered at a ventricular lower rate (LR) pacing interval that is independent of atrial events and does not track the atrial rate. Generally, an atrial tracking ventricular pacing mode is desirable when the sinus node of the heart is functioning normally in setting the intrinsic atrial rate or the atria are being paced at an appropriate pacing rate for the patient's level of physical activity.

Under some circumstances, however, it is undesirable to track the atrial rate, e.g., during atrial tachyarrhythmia such as atrial fibrillation or atrial flutter. As such, a method for switching between an atrial tracking ventricular pacing mode and a non-atrial tracking ventricular pacing mode is desirable. An intracardiac ventricular pacemaker is disclosed herein that delivers ventricular pacing that tracks the atrial rate at appropriate times and does not track the atrial rate at times that atrial tracking is not appropriate. In this way, ventricular pacing is provided based on the patient's need and in a manner that does not result in pacemaker mediated ventricular tachycardia.

An intracardiac ventricular pacemaker as disclosed herein may have a motion sensor for detecting atrial systolic mechanical events. During the atrial tracking pacing mode, the AV pacing interval is started in response to detecting the atrial systolic mechanical event. Atrial systolic mechanical event detection during one or both the atrial tracking pacing mode and the non-atrial tracking pacing mode may be used to determine if pacing mode switching criteria are met for controlling when the pacemaker switches between the atrial tracking pacing mode and the non-atrial tracking pacing mode. During the non-atrial tracking pacing mode, the ventricular intracardiac pacemaker may determine an activity level of the patient from the motion sensor signal to provide rate responsive ventricular pacing at a temporary LR pacing interval that is adjusted to meet the demand of the patient's physical activity. Techniques are disclosed herein for controlling switching between an atrial tracking ventricular pacing mode and a non-atrial tracking ventricular pacing mode based on the motion sensor signal in an ventricular intracardiac pacemaker. As described below, the ventricular intracardiac pacemaker limits the maximum ventricular pacing rate during the non-atrial tracking ventricular pacing mode, e.g., a VVIR pacing mode, based on the timing of cardiac events detected from the motion sensor signal.

FIG. 1 is a conceptual diagram illustrating an intracardiac pacing system 10 that may be used to sense cardiac electrical signals and motion signals induced by patient physical activity, cardiac motion and flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 may be transcatheter intracardiac pacemakers which may be adapted for implantation wholly within a heart chamber, e.g., wholly within the RV, wholly within the left ventricle (LV), wholly within the RA or wholly within the left atrium (LA) of heart 8.

In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, a ventricular intracardiac pacemaker 14 may be positioned in the LV and configured to detect cardiac motion signals and deliver atrial-synchronized ventricular pacing to the LV using the techniques disclosed herein. Pacemaker 14 may be positioned within the right ventricle or left ventricle to provide respective right ventricular or left ventricular pacing and for sensing motion signals by a motion sensor within the ventricular chamber. Pacemaker 12 may be positioned outside or within the right atrium or left atrium to provide respective right atrial or left atrial pacing. Pacemakers 12 and 14 may be reduced in size compared to subcutaneously implanted pacemakers and may be generally cylindrical in shape to enable transvenous implantation via a delivery catheter.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. RV pacemaker 14 is configured to deliver RV pacing pulses and sense an RV cardiac electrical signal using housing based electrodes for producing an RV EGM signal. The cardiac electrical signals may be sensed by the respective pacemaker 12 or 14 using the housing based electrodes that are also used to deliver pacing pulses to the respective RA or RV.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA contraction and the RV contraction, e.g., by maintaining a target AV pacing interval between atrial events, which may be sensed from the motion signal, and ventricular pacing pulses. That is, the RV pacemaker 14 controls RV pacing pulse delivery to maintain a desired AV interval between an atrial activation corresponding to atrial systole (intrinsic or pacing-evoked) and the subsequent ventricular pacing pulse delivered to cause ventricular depolarization.

According to the techniques described herein, atrial activations are detected by RV pacemaker 14 from a motion sensor signal that includes motion signals caused by ventricular and atrial events. For example, acceleration of blood flowing into the RV through the tricuspid valve 16 between the RA and RV caused by atrial contraction, sometimes referred to as the "atrial kick," is detected by RV pacemaker 14 from the signal produced by a motion sensor, for example an accelerometer, included in RV pacemaker 14. Other cardiac motion signals that may be detected by RV pacemaker 14 are described below in conjunction with FIG. 4 and may include motion caused by ventricular contraction, motion caused by ventricular relaxation, and motion caused by passive filling of the ventricle.

Atrial P-waves that are attendant to atrial depolarization are relatively low amplitude, far-field signals in the RV cardiac electrical signal received by pacemaker 14 compared to the amplitude of near-field R-waves. The far-field P-wave can be difficult to reliably detect from the cardiac electrical signal acquired by RV pacemaker 14. As such, atrial-synchronized ventricular pacing by RV pacemaker 14 may not be reliable when atrial events are sensed solely from a cardiac electrical signal received by RV pacemaker 14. According to the techniques disclosed herein, the RV pacemaker 14 includes a motion sensor, such as an accelerometer, and is configured to detect an atrial systolic event corresponding to the mechanical activation (contraction) of the atria present in the motion signal produced by the motion sensor. Ventricular pacing pulses are synchronized to the atrial event that is detected from the motion signal by setting a programmable AV pacing interval in response to detecting the atrial systolic event. The AV pacing interval controls the timing of the ventricular pacing pulse relative to the detected atrial systolic event. Detection of the atrial systolic event used to synchronize ventricular pacing pulses to atrial systolic events may include detection of other cardiac event motion signals, e.g., ventricular events, in order to positively identify the atrial systolic event.

A target AV interval may be a programmed value selected by a clinician and is the time interval from the detection of the atrial event from the motion sensor signal until delivery of the ventricular pacing pulse. In some instances, the target AV interval may be started from the time the atrial systolic event is detected from a motion sensor signal or starting from an identified fiducial point of the atrial systolic event signal in the motion sensor signal. The target AV interval may be identified as being hemodynamically optimal for a given patient based on clinical testing or assessments of the patient or based on clinical data from a population of patients.

Pacemakers 12 and 14 may each be capable of bidirectional wireless communication with an external device 20 for programming the AV pacing interval and other pacing control parameters as well as mechanical event sensing parameters utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters and pacing mode switching criteria, may be programmed into pacemaker 14 using external device 20.

External device 20 is configured for bidirectional communication with implantable telemetry circuitry included in RV pacemaker 14 and RA pacemaker 12 (when present). External device 20 may establish a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from pacemaker 14 or pacemaker 12, motion sensor signals acquired by pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14, e.g., after viewing a visual representation of EGM, motion sensor signal and marker channel data.

Pacemaker 12 and pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses in a respective heart chamber. As disclosed herein, RV pacemaker 14, however, is configured to detect atrial events as often as beat-by-beat from a motion sensor signal, without requiring communication signals from RA pacemaker 12. Atrial event detection for controlling atrial-synchronized ventricular pacing and for determining when to switch to a non-atrial tracking pacing mode, e.g., a VVIR pacing mode, is performed by RV pacemaker 14.

Figure 2A:
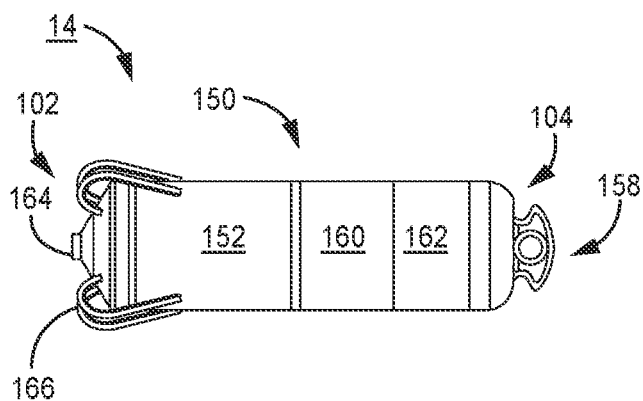
FIG. 2A is a conceptual diagram of the intracardiac ventricular pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location within a ventricular heart chamber during an implantation procedure.

Figure 2B:
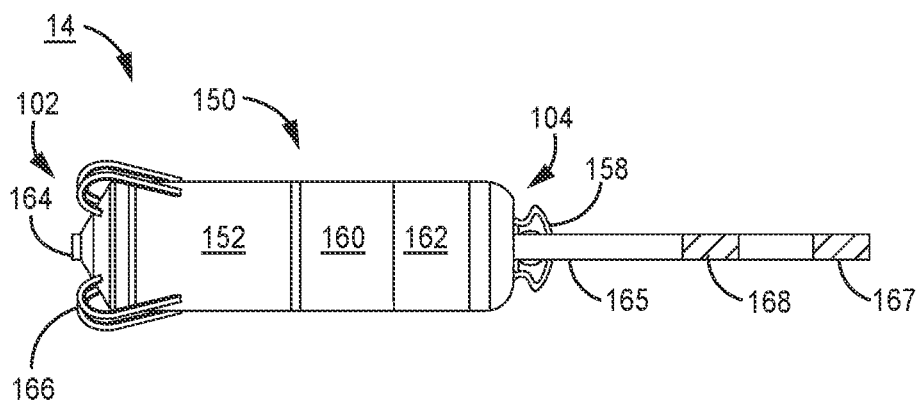
FIG. 2B is a conceptual diagram of another example of the intracardiac ventricular pacemaker shown in FIG. 1.

FIG. 2B is a conceptual diagram of another example of RV pacemaker 14. In FIG. 2B, RV pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 167 or 168 which may be paired with distal electrode 164 at an increased inter-electrode distance compared to the inter-electrode spacing of housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
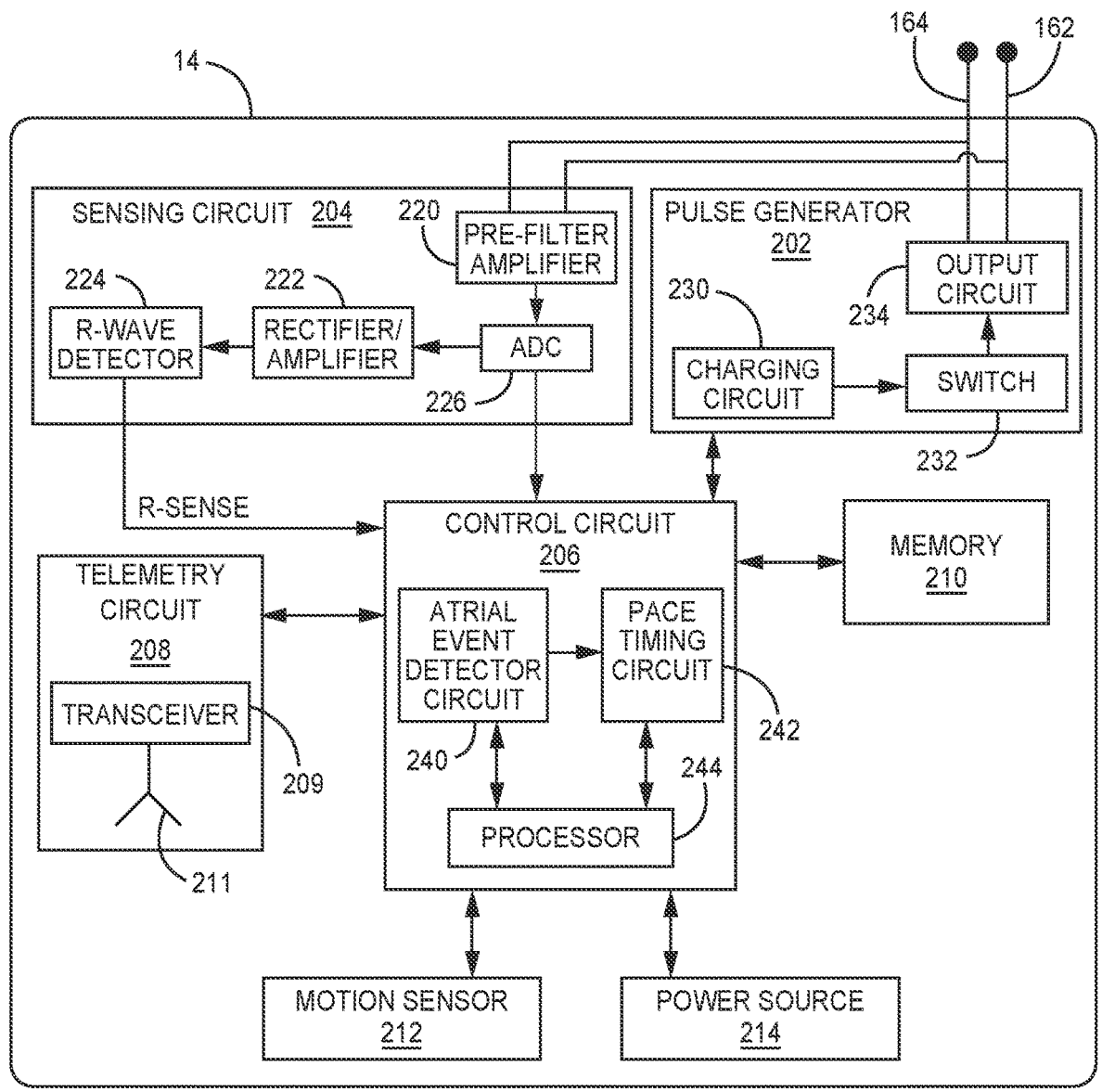
FIG. 3 is a schematic diagram of an example configuration of the pacemaker of FIG. 2A.

FIG. 3 is a schematic diagram of an example configuration of pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in pacemaker 14 include piezoelectric sensors and micro electro-mechanical systems (MEMS) devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and in U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events from a motion signal using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

In addition to being subjected to cardiac motion, the motion sensor 212 is subjected to patient body motion during physical activity such as walking, driving, exercise, changing body posture, household chores and other activities of daily living. The motion sensor signal may be used by control circuit 206 for detecting cardiac mechanical events as described in greater detail below as well as determining the patient's body posture and/or a metric of patient physical activity. Techniques for monitoring patient body posture and patient physical activity from an accelerometer signal are generally disclosed in the above-incorporated references. While examples presented herein refer to a single motion sensor, it is recognized that motion sensor 212 may be implemented as two or more individual motion sensors with one motion sensor providing a signal from which a patient activity metric is determined and another motion sensor providing a signal from which atrial events are detected.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (Rsense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 may include an atrial event detector circuit 240, pace timing circuit 242, and processor 244. Atrial event detector circuit 240 is configured to detect atrial mechanical events from a signal received from motion sensor 212. As described below, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. R-wave sensed event signals may also be passed to atrial event detector circuit 240 for use in setting ventricular event detection windows and/or atrial event refractory periods.

Atrial event detector circuit 240 receives a motion signal from motion sensor 212 and may start an atrial refractory period in response to a ventricular electrical event, e.g., an R-wave sensed event signal from sensing circuit 204 or delivery of a pacing pulse by pulse generator 202. Atrial event detector circuit 240 may be configured to determine if the motion sensor signal satisfies atrial mechanical systolic event detection criteria outside of the refractory period. The motion sensor signal during the refractory period may be monitored by atrial event detector circuit 240 for the purposes of detecting ventricular mechanical events, which may be used for confirming or validating atrial systolic event detection and/or setting atrial systolic event detection control parameters. As such, ventricular mechanical event detection windows may be set during the atrial refractory period and may be set according to predetermined time intervals following identification of a ventricular electrical event. The timing and detection of the ventricular mechanical events may be used to update the atrial refractory period and/or an atrial systolic detection threshold amplitude and may be used to confirm detection of the atrial systolic event occurring subsequent to ventricular mechanical events.

Atrial event detector circuit 240 may pass an atrial event detection signal to processor 244 and/or pace timing circuit 242. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. Techniques for controlling atrial-synchronized ventricular pacing using a motion sensor signal are generally disclosed in U.S. Pat. No. 9,399,140, (Yong, et al.), incorporated herein by reference in its entirety.

Pace timing circuit 242 may additionally include a LR pacing interval timer for controlling a minimum ventricular pacing rate in the absence of detected atrial events. For example, if an atrial systolic event is not detected from the motion sensor signal triggering a ventricular pacing pulse at the programmed AV pacing interval, a ventricular pacing pulse may be delivered by pulse generator 202 upon expiration of the LR pacing interval to prevent ventricular asystole and maintain a minimum ventricular rate.

During a non-atrial tracking pacing mode, the LR pacing interval timer is used to control the rate of ventricular pacing pulses that are delivered independent of the atrial rate. The LR pacing interval may be set to a minimum or base LR pacing interval to maintain a minimum ventricular rate and may be adjusted to a temporary LR pacing interval to provide rate responsive pacing. A sensor indicated rate (SIR) (also referred to herein as a sensor indicated pacing interval) may be determined based on the patient's physical activity level. In some instances, the SIR may be determined from the motion sensor signal received from motion sensor 212. In other examples, an SIR may be determined by another sensor, such as a temperature sensor or the like. A temporary LR pacing interval set based on a sensor indicated rate (SIR) provides ventricular pacing pulses at a rate greater than the minimum or base pacing rate.

The higher ventricular rate support is provided according to the patient's metabolic demand during periods of non-resting physical activity based on the SIR. The use of an accelerometer in an intracardiac pacemaker for obtaining a patient activity signal is generally disclosed in U.S. Pat. No. 9,814,887 (Nikolski, et al.), incorporated herein by reference in its entirety. The use of a patient activity signal for determining a SIR and providing rate-responsive pacing is generally disclosed in U.S. Pat. No. 5,720,769 (van Oort) and U.S. Pat. No. 7,031,772 (Condie, et al.), both incorporated herein by reference in its entirety.

Processor 244 may retrieve other programmable pacing control parameters, such as pacing pulse amplitude and pacing pulse width that are passed to pulse generator 202 for controlling pacing pulse delivery. In addition to providing control signals to pace timing circuit 242 and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240 for use in detecting and confirming atrial systolic events, e.g., ventricular event detection windows, atrial refractory period, detection threshold amplitudes applied to the motion sensor signal, and any other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or LR pacing interval during a non-atrial tracking pacing mode) and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the ventricular pacing mode and delivery of pacing pulses by pulse generator 202.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity. However, power source 214 is to be understood to provide power to pulse generator 202, sensing circuit 204, telemetry circuit 208, memory 210, motion sensor 212 and control circuit 206 as needed. For example, power source 214 may provide power to the charging circuit 230 for charging one or more holding capacitors and to switching circuit 232 for controlling the discharge of the holding capacitors through output circuit 234.

Telemetry circuit 208 includes a transceiver 209 and antenna 211 for transferring and receiving data, e.g., via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial and ventricular event detection from the motion sensor signal and for ventricular pacing control may be received by telemetry circuit 208 and stored in memory 210 for access by control circuit 206.

Figure 4:
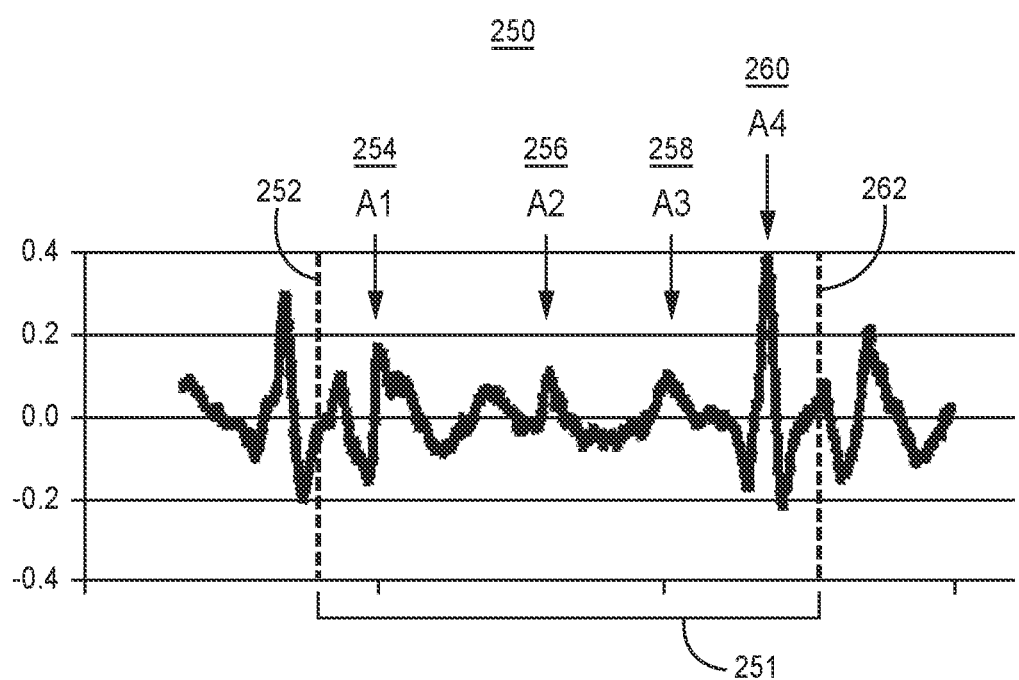
FIG. 4 is an example of a motion sensor signal that may be acquired over a cardiac cycle by a motion sensor included in the ventricular intracardiac pacemaker of FIG. 1.

FIG. 4 is an example of a motion sensor signal 250 that may be acquired by motion sensor 212 over a cardiac cycle. Vertical dashed lines 252 and 262 denote the timing of two consecutive ventricular events (intrinsic ventricular depolarizations and/or ventricular pacing pulses), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 250 is implemented as an accelerometer) that occurs during ventricular contraction and marks the approximate onset of ventricular mechanical systole. The A1 event is also referred to herein as a "ventricular contraction event." The A2 event 256 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial systolic event" or merely the "atrial event." The A4 event 260 is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260 when pacemaker 14 is operating in an atrial tracking ventricular pacing mode. Control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses. Various techniques for A4 event detection, controlling the AV pacing interval during an atrial-tracking ventricular pacing mode based on A4 events, and switching between atrial-tracking and non-atrial tracking ventricular pacing mode based on a motion sensor signal are generally disclosed in U.S. patent application Ser. No. 15/280,538 (Splett, et al), U.S. patent application Ser. No. 15/280,339 (Sheldon, et al.), U.S. patent application Ser. No. 15/366,993 (Sheldon et al.), and U.S. patent application Ser. No. 15/377,717 (Demmer et al.), all of which are incorporated herein by reference in their entirety.

As the heart rate increases, the time between the A3 and A4 events may decrease and the A3 and A4 events may merge and become difficult to distinguish in the motion sensor signal. As a result, detection of the A4 events by RV pacemaker 14 for setting an AV pacing interval to provide atrial tracking of the ventricular pacing pulses may become compromised. RV pacemaker 14 may be configured to switch from the atrial tracking ventricular pacing mode to a non-atrial tracking ventricular pacing mode if the A4 event is not being detected or a condition is detected that is associated with unreliable A4 event sensing, e.g., a high heart rate or high level of patient activity. For example RV pacemaker 14 may switch from a VDDR pacing mode to a VVIR pacing mode in response to pacing mode switching criteria being satisfied. During the VVIR pacing mode RV pacemaker 14 may determine a SIR and adjust the ventricular LR pacing interval from a base rate interval to a temporary LR interval set according to the SIR. As the ventricular pacing rate is increased, however, the ventricular pacing pulse may be delivered during the passive or active filling phase of the ventricle, which may cause an undesirable decrease in cardiac output. In order to prevent the ventricular pacing pulse from being delivered too early during ventricular filling, a minimum limit of the temporary LR interval may be established to limit the maximum rate responsive pacing rate during a non-atrial tracking ventricular pacing mode.

Figure 5:
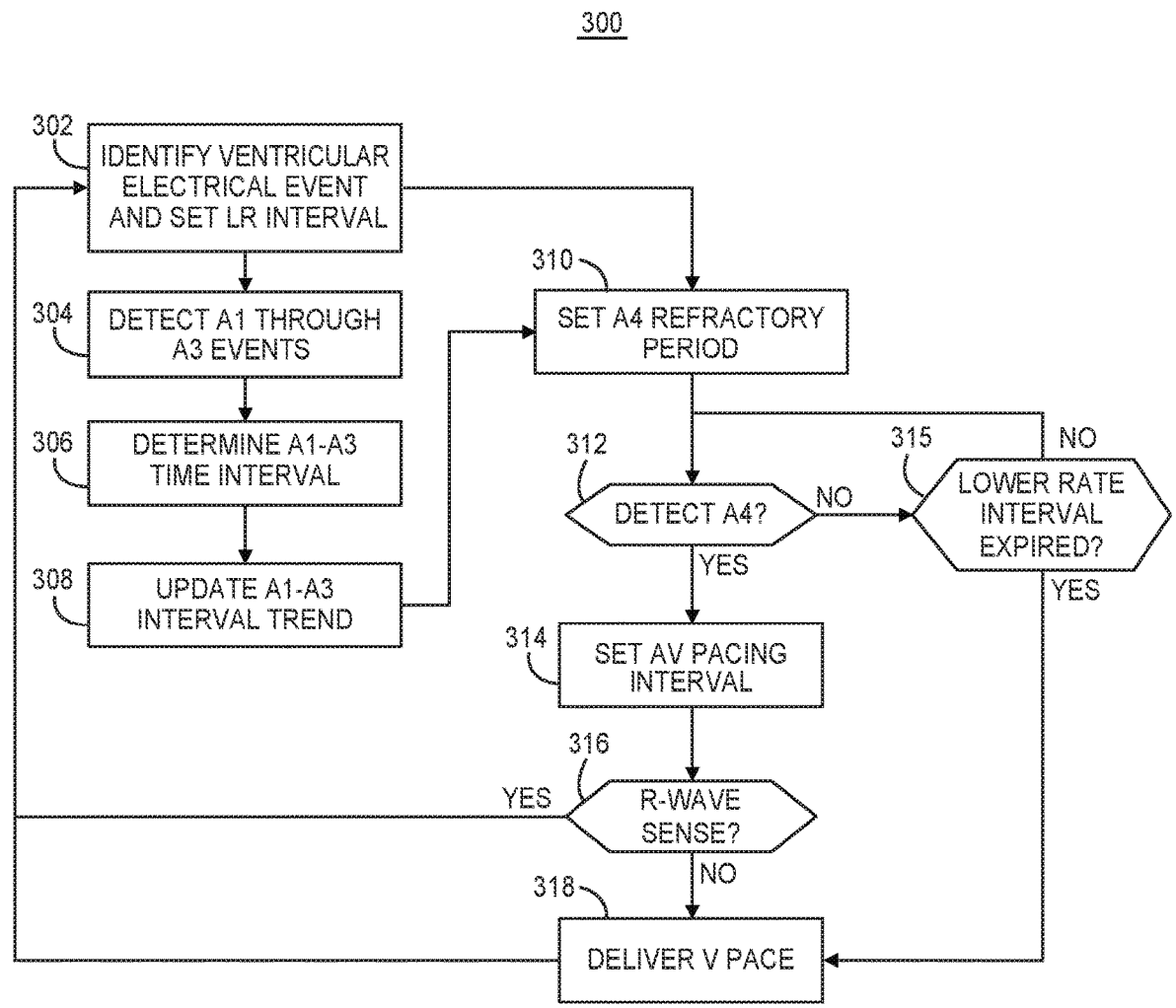
FIG. 5 is a flow chart of one method performed by an intracardiac ventricular pacemaker for detecting the A4 event and controlling ventricular pacing during an atrial tracking pacing mode.

FIG. 5 is a flow chart 300 of one method performed by pacemaker 14 for detecting the A4 event and controlling ventricular pacing during an atrial tracking pacing mode. At block 302, control circuit 206 identifies a ventricular event. The ventricular event may be an R-wave sensed event signal received from sensing circuit 204 or a ventricular pacing pulse delivered by pulse generator 202. Since the ventricular A1, A2 and A3 events may have different characteristics during an intrinsic ventricular rhythm than during a ventricular paced rhythm, the methods described herein for determining amplitudes, time intervals or other characteristics of the A1, A2 and A3 events for use in setting A4 detection control parameters or confirming A4 event detection may be determined for both an intrinsic ventricular rhythm and a ventricular paced rhythm.

For example, as described in conjunction with the flow charts and timing diagrams presented herein, various time intervals, sensing windows, atrial refractory period, and atrial event detection threshold amplitude may be set based on characterizations of one or more of the A1, A2 and A3 events. One set of A4 detection control parameters and characteristics of the A1, A2 and A3 events may be determined and stored for use during episodes of ventricular sensing (ventricular intrinsic rhythm), and another set of A4 detection control parameters and characteristics of the A1, A2 and A3 events may be determined and stored for use during episodes of ventricular pacing.

During ventricular sensing, control circuit 206 may be configured to discriminate a normal sinus R-wave from a premature ventricular contraction (PVC) so that ventricular events identified at block 302 for use in starting a search for the A1 through A4 events from the motion sensor signal do not include PVCs. When a ventricular event, sensed or paced, is identified at block 302 that is not a PVC, pace timing circuit 242 may set an escape interval timer to a ventricular LR pacing interval. If the LR pacing interval expires (as described below in conjunction with block 315), a ventricular pacing pulse may be delivered, asynchronous to atrial activity, in order to maintain some minimum, base ventricular rate.

At block 304, atrial event detector 240 detects the A1 through A3 motion signals. Briefly, atrial event detector 240 may compare the motion sensor signal to one or more predetermined detection threshold amplitudes during one or more time windows set in response to identifying the ventricular event at bock 302 for detecting the A1 through A3 events. In some examples, the A4 event may also be detected at block 304 to increase confidence in the positive identification of each of the four motion sensor signals A1 through A4 in a given cardiac cycle. In this example, the A1 through A3 events, and optionally A4, may be detected on a beat-by-beat basis.

After the A1 through A3 events are detected, the A1-A3 time interval is determined at block 304 as the time interval from the A1 event detection to the A3 event detection. The A1-A3 time interval may be used to update an A1-A3 interval trend at block 308. For example, a running average A1-A3 time interval may be updated at block 308 using the most recent N A1-A3 time interval measurements, e.g., the most recent three to twelve A1-A3 time intervals.

The A1-A3 time interval is used to set a post-ventricular atrial refractory period at block 310. This atrial refractory period is also referred to herein as an "A4 refractory period" because A4 event detection may be inhibited or ignored during the atrial refractory period in some examples. When a ventricular electrical event is identified at block 302, atrial event detector 240 may start the atrial refractory period at block 310. The atrial refractory period may be set based on the A1-A3 time interval, e.g., to a percentage longer than or a fixed interval longer than the A1-A3 time interval. For example, the atrial refractory period may be set to be 50 to 150 ms longer than the A1-A3 time interval, though shorter or longer fixed intervals may be added to the A1-A3 time interval for setting the atrial refractory period. The fixed time interval used to set the atrial refractory period may vary depending on heart rate in some examples.

During the atrial refractory period, any motion sensor events that are detected, or cross a detection threshold amplitude, are ignored for the purposes of triggering a ventricular pacing pulse and starting an AV pacing interval. Ventricular mechanical events A1 through A3 may be detected during the atrial refractory period, as indicated at block 304, to determine the A1-A3 time interval and update the A1-A3 interval trend (blocks 306 and 308), either periodically or on a beat-by-beat basis.

At block 312, atrial event detector circuit 240 monitors the motion sensor signal to detect the A4 event after the expiration of the atrial refractory period. If the A4 event is not detected before the LR pacing interval expires (block 315), a ventricular pacing pulse is delivered at block 316 to ensure a minimum ventricular rate, e.g., at least 40 to 60 beats per minute (bpm). Furthermore, it is to be understood that if an intrinsic R-wave is sensed before an A4 event is detected, the process of FIG. 5 may return to block 302 where the sensed R-wave is identified as a ventricular electrical event, and control circuit 206 restarts the process of detecting the A4 event on the next ventricular cycle.

If the A4 event is detected before the LR pacing interval expires, control circuit 206 sets the AV pacing interval at block 314 in response to detecting the A4 event. If an intrinsic R-wave is not sensed from the cardiac electrical signal by sensing circuit 204 during the AV pacing interval, "no" branch of block 316, a ventricular pacing pulse is delivered by pulse generator 202 at block 318 upon expiration of the AV pacing interval. The ventricular pacing pulse, if delivered, and otherwise the sensed R-wave, is identified as the next ventricular event at block 302 and the process repeats.

In this way, the A1 through A3 events may be detected from the motion sensor signal on a beat-by-beat (or less frequent) basis for updating the A1-A3 time interval trend used to set the atrial refractory period to provide a high likelihood of positively detecting the A4 event and properly timing a ventricular pacing pulse in synchrony with the atrial event. Other motion sensor signal events A1 through A3 are unlikely to be falsely detected as the A4 event by applying the atrial refractory period set based on the A1-A3 timing.

In some examples, rather than determining an A1-A3 time interval, a time interval to the A2 event may be determined so that the atrial refractory period is set based on the A1-A2 time interval to extend through at least the A2 event and expire before the A3 event. In this example, an A4 detection threshold amplitude may be set higher than an expected A3 event amplitude to allow detection of the A4 event earlier in the ventricular cycle, for example as the atrial rate is increasing. In other cases, the time interval from the identified ventricular electrical event to the A1, A2 or A3 event may be determined and used in setting the atrial refractory period.

In some examples, the process of blocks 304 through 308 is performed periodically rather than on a beat-by-beat basis. For example detection of A1-A3 events during the atrial refractory period may occur on every third cardiac cycle, every eighth cardiac cycle, once per minute, or other predetermined schedule for updating the A1-A3 time interval (or other ventricular event time interval as discussed above) used for setting the atrial refractory period at block 310. In some cases, the heart rate, paced or intrinsic, may be monitored and the A1-A3 events may be detected for updating the A1-A3 interval trend when the heart rate changes by more than a predetermined amount. For example, ventricular event intervals between consecutive ventricular events may be determined upon identifying ventricular events at block 302. The ventricular event intervals may be RR intervals between consecutively sensed intrinsic R-waves or VV intervals between consecutively delivered ventricular pacing pulses and may include RV intervals between a sensed intrinsic R-wave and a consecutively delivered pacing pulse and VR intervals between a delivered pacing pulse and a consecutively sensed R-wave. Both the intrinsic heart rate and the paced rate may change, e.g., when pacemaker 14 is a rate responsive pacemaker. If the ventricular event interval changes or a trend in the ventricular event interval changes by more than a predetermined amount, the control circuit may perform blocks 304 through 308 to update the A1-A3 interval trend used for setting the atrial refractory period.

In other examples, if the A4 event is not detected at block 312 after the atrial refractory period and before the next ventricular event (intrinsic or paced) is identified at block 302, the control circuit 206 may perform the process of blocks 304 through 306 for a predetermined number of consecutive or non-consecutive cardiac cycles to update the A1-A3 interval trend used to set the atrial refractory period to restore A4 detection.

Figure 6:
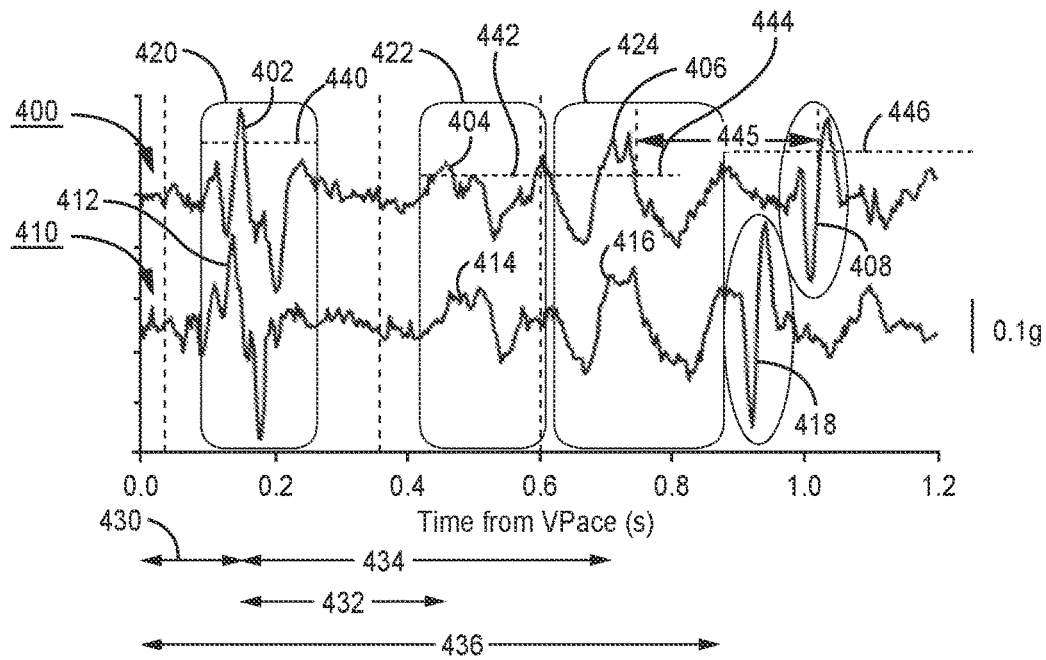
FIG. 6 is an example of motion sensor signals acquired over two different cardiac cycles.

FIG. 6 is an example of motion sensor signals 400 and 410 acquired over two different cardiac cycles and obtained within a beating heart. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring during ventricular relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave. However during a stable paced or intrinsic ventricular rhythm the relative timing of A1, A2 and A3 events to each other and the immediately preceding ventricular electrical event is expected to be consistent for a given heart rate.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining the atrial refractory period and increasing confidence in reliably detecting A4 events 408 and 418. The timing of the A1 through A3 events, particularly an A3 time interval since a ventricular electrical event, may also be used for establishing a minimum temporary LR interval during rate responsive pacing in a non-atrial tracking ventricular pacing mode. In some examples, an A1 sensing window 420 may be set based on an expected Vpace-A1 time interval. The Vpace-A1 time interval 430 may be measured when the motion sensor signal 400 or 410 crosses an A1 sensing threshold amplitude 440. The A1 sensing window 420 may be adjusted on the next cardiac cycle based on the Vpace-A1 time interval 430 determined on the current cardiac cycle or a running average Vpace-A1 time interval.

An A2 sensing window 422 may be set based on an expected Vpace-A2 time interval (not explicitly shown but understood to be the total time from 0.0 seconds to an A2 event detection) or an A1-A2 time interval 432 (time from A1 detection to time of A2 detection). The A2 event 404 or 414 may be detected at the time of the first positive-going crossing of an A2 sensing threshold amplitude 442 by the motion sensor signal 400 or 410 during the A2 sensing window 422. The A2 sensing window 422 may be adjusted on the next cardiac cycle based on the Vpace-A2 time interval or A1-A2 time interval 432 determined on the current cardiac cycle.

Similarly, an A3 sensing window 424 may be set based on an expected Vpace-A3 time interval (not explicitly labeled but understood to be sum of time intervals 430 and 434), A1-A3 time interval 434, or A2-A3 time interval (not explicitly labeled but understood to be the time interval from the sensed A2 event 404 or 414 to the sensed A3 event 406 or 416). The A3 event 406 or 416 may be detected during the A3 sensing window 424 when the motion sensor signal 400 or 410, respectively, crosses an A3 sensing threshold amplitude 444. The threshold crossing resulting in an A3 event detection may be the first positive going threshold crossing, the last negative going threshold crossing (of a rectified signal) or another fiducial point of the A3 event signal. The A3 sensing window 424 may be adjusted on the next cardiac cycle based on the Vpace-A3 time interval, A1-A3 time interval 434, or the A2-A3 time interval determined during the current cardiac cycle.

Each of the sensing windows 420, 422 and 424 may be set based on a history of time intervals determined from a ventricular pacing pulse or sensed intrinsic R-wave to the respective A1 event 402 or 412, A2 event 404 or 414 and A3 event 406 or 416 or based on a history of time intervals between the detected A1, A2 and A3 events or any combination thereof. For example, the A2 sensing window 422 may be set to start based on time intervals measured between a ventricular pacing pulse or sensed R-wave and the detected A1 event. The end of the A2 sensing window 422 may be set to start based on an A1-A2 time interval 432 or based on an A1-A3 time interval 434. It is recognized that numerous methods may be conceived for setting the A1, A2 and A3 sensing windows 420, 422 and 424, respectively, based on the consistency of the expected time intervals between any combinations of the ventricular electrical event (paced or sensed) and subsequent A1, A2 and A3 events. Furthermore, it is contemplated that these sensing windows 420, 422 and 424 may be set according to different control parameters, such as different fixed time intervals added to or subtracted from measured event time intervals depending on whether the ventricular electrical event is a paced or sensed event and/or depending on heart rate. The event time intervals that may be measured and used for setting the onset, offset and duration of the sensing windows 420, 422 and 424 may include any one or combination of the Vpace-A1, Vpace-A2, Vpace-A3, Rsense-A1, Rsense-A2, Rsense-A3, A1-A2, A1-A3, and/or A2-A3 time intervals determined during a paced and/or intrinsic rhythm.

The sensing threshold amplitudes 440, 442 and 444 may be set uniquely during each of the respective sensing windows 420, 422 and 424, respectively, or set to a fixed common value for all sensing windows. The sensing threshold amplitudes 440, 442, and 444 may be fixed or decaying thresholds and may be automatically adjusted thresholds set to starting threshold values based on the peak motion sensor signal amplitude detected during each respective window 420, 422 and 424. The motion sensor signals 400 and 410 are shown as raw signals, but the motion sensor signal may be filtered, amplified and rectified by circuitry included in motion sensor 212 to provide control circuit 206 with a rectified signal that is used to detect the A1 through A4 events.

A post-ventricular, atrial refractory period 436 may be set based on the A1-A3 time interval 434 or based on the sensed R-wave-A3 or Vpace-A3 time interval (sum of Vpace-A1 interval 430 and A1-A3 time interval 434). In some examples, the atrial refractory period 436 ends upon the expiration of the A3 sensing window 424. In other examples, the atrial refractory period 436 ends after the expiration of the A3 sensing window 424. The A4 event 408 or 418 may be detected in response to a crossing of an A4 sensing threshold amplitude 446, e.g., the first positive-going crossing or a last negative-going crossing, by the rectified motion sensor signal outside the atrial refractory period 436.

In some examples, the A4 detection is confirmed when the A1, A2 and A3 events have each been detected during the atrial refractory period 436. If any one of the A1, A2 or A3 events was not detected during the atrial refractory period 436, the A4 event detection based on a crossing of threshold 446 may not be confirmed and not used for starting an AV pacing interval. In other examples, at least one of the A1, A2 or A3 events may be required to be detected during a respective sensing window 420, 422, or 424 on a beat-by-beat basis for confirming an A4 detection after the atrial refractory period 436.

The A1, A2 and/or A3 events sensed during the respective A1 sensing window 420, A2 sensing window 422 and A3 sensing window 424 may be used for updating the atrial refractory period 436 as described in conjunction with FIG. 5 on a beat-by-beat or less frequent basis without requiring positive detection of each of A1, A2, and/or A3 for confirming an A4 detection on each beat. Setting the atrial refractory period based on detection and relative timing of the A1 through A3 events enables the atrial refractory period to be set based on the consistent timing of the ventricular motion sensor signal events so that A4 events may be detected with high reliability even when the timing of the A4 event relative to the A1-A3 events and the preceding ventricular electrical event is variable. A3 event detection may additionally or alternatively be used for determining an A3 time interval and establishing a minimum LR pacing interval used during the non-atrial tracking ventricular pacing mode. The A3 time interval may be determined during the atrial tracking ventricular pacing mode and used during the non-atrial tracking ventricular pacing mode for limiting the minimum temporary LR pacing interval during rate responsive pacing.

In some examples, an A3-A4 event interval 445 is determined and used for adjusting the A4 refractory period 436. For example, the A3 event 406 may be detected by detecting the last, negative-going crossing of an A3 event detection threshold amplitude 444 during the A3 sensing window 424. The A4 event 408 may be detected by the first positive-going crossing of the A4 event detection threshold amplitude 446 after the expiration of the A4 refractory period 436. The A3-A4 event interval 445 is determined as the time from the A3 event detection and the time of the A4 event detection. This A3-A4 event time may be compared to a previous A3-A4 event time, e.g., compared to one or more preceding A3-A4 event times which may be determined during the respective one or more preceding cardiac cycles or to a running average A3-A4 event time determined from two to five or other predetermined number of previously determined A3-A4 event times. If a change in the A3-A4 event time interval compared to one or more preceding A3-A4 event times is detected, the A4 refractory period 436 may be adjusted. As the A3-A4 event time is detected to shorten or increase, the control circuit 206 may decrease or lengthen the A4 refractory period, respectively, to account for changes in the time interval between the ventricular diastolic event and the atrial systolic event as the atrial rate changes.

Figure 7:
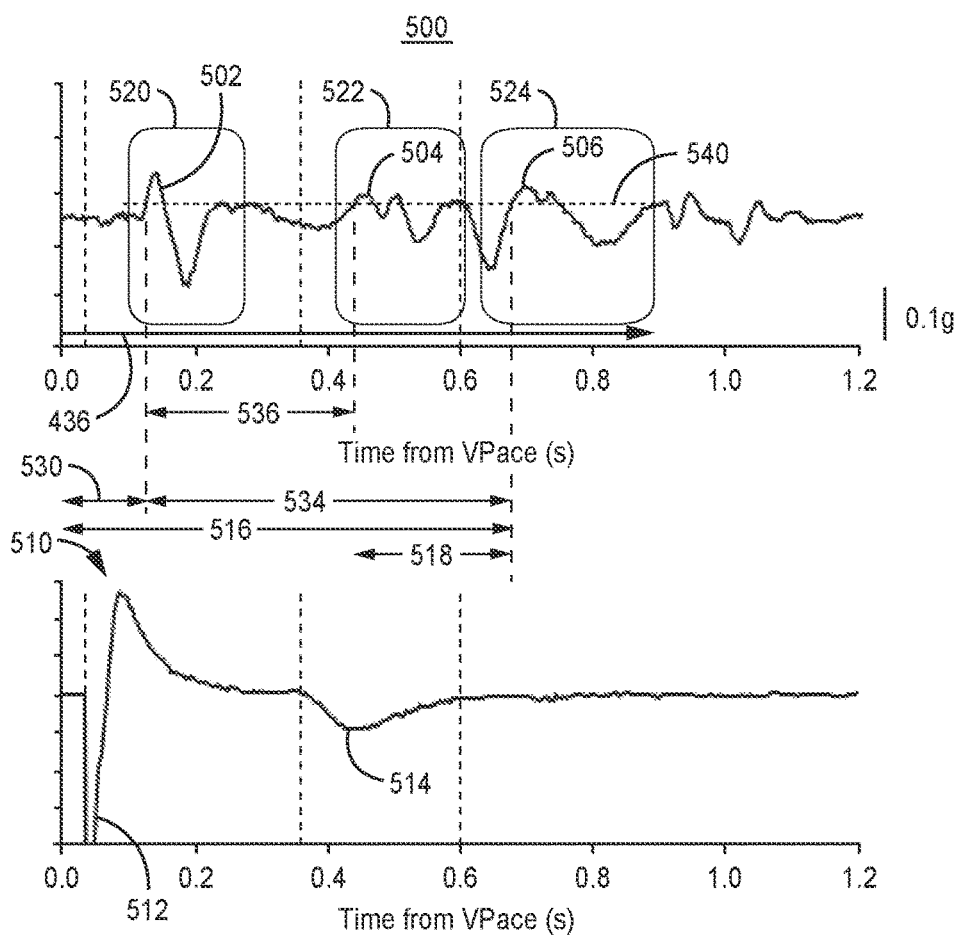
FIG. 7 is an averaged motion sensor signal that may be determined by averaging the motion sensor signal obtained over multiple cardiac cycles.

FIG. 7 is an averaged motion sensor signal 500 that may be determined by control circuit 206 by averaging the motion sensor signal obtained over multiple cardiac cycles, e.g., signals 400 and 410 of FIG. 6. The averaged motion sensor signal 500 may represent the average of 3 to 20 or other predetermined number of cardiac cycles. The raw motion sensor signal or a filtered, amplified and/or rectified motion sensor signal may be buffered beginning from a ventricular electrical event, pacing pulse or sensed R-wave, at time 0.0 seconds until the next ventricular electrical event. The buffered motion sensor signal obtained over one cardiac cycle may be averaged with the buffered motion sensor signals obtained over a predetermined number of other cardiac cycles to produce averaged motion sensor signal 500.

A ventricular electrical signal 510 is shown aligned in time with averaged motion sensor signal 500. Ventricular electrical signal 510 may be passed from sensing circuit 204 to control module 206 and includes an R-wave 512, which may be an evoked or intrinsic R-wave, and a T-wave 514. R-wave 512 is followed by the ventricular contraction A1 event 502. The ventricular relaxation A2 event 504 occurs during T-wave 514. The passive ventricular filling A3 event 506 occurs after T-wave 514.

Since the A1, A2 and A3 events are ventricular mechanical events, they occur at consistent time intervals relative to each other and relative to ventricular electrical events (R-wave 512 and T-wave 514). As a result, the signal-to-noise ratio of the A1 signal 502, A2 signal 504 and A3 signal 506 is improved in the averaged motion sensor signal 500 compared to the single-cycle motion sensor signals 400 and 410 of FIG. 6. The averaged A1 event 502, A2 event 504 and A3 event 506 have an improved signal-to-noise ratio compared to the A1, A2 and A3 events observed in the motion sensor signal 400 or 410 of a single cardiac cycle as shown in FIG. 6, making A1, A2, and A3 event detection from the averaged motion signal 500 more reliable.

A single event detection threshold amplitude 540 may be defined such that the a crossing of the threshold 540 by the averaged, rectified motion sensor signal 500 within the A1 sensing window 520, A2 sensing window 522 and A3 sensing window 524 is detected as the respective A1 event 502, A2 event 504, and A3 event 506. The threshold crossing may be a first, positive-going crossing or a last, negative-going crossing in various examples. Alternatively, unique detection threshold amplitudes may be defined for each sensing window 520, 522 and 524 for detecting the respective A1, A2 and A3 events. The sensing windows 520, 522 and 524 may be initially set according to expected A1, A2 and A3 event timing following the ventricular pacing pulse or R-wave 512 and may be adjusted according to the actual detection time of each respective A1 event 502, A2 event 504, and A3 event 506 based on a threshold crossing. The sensing windows 520, 522 and 524 may be set based on ventricular pacing rate or atrial event rate, e.g., based on A4-A4 event intervals. The sensing windows 520, 522 and 524 may also be set differently following a ventricular pacing pulse than following an intrinsic R-wave sensed event since the timing of the A1, A2 and A3 events and T-wave 514 may be altered during ventricular pacing compared to during an intrinsic ventricular rhythm.

The atrial systolic A4 event timing, which is independent of the ventricular electrical event timing, may be more variable from one cardiac cycle to the next with respect to the ventricular electrical and mechanical events, e.g., as shown by the relative timing of the A4 events 408 and 418 of signals 400 and 410 (FIG. 6). As a result, the A4 signal is largely attenuated in the averaged motion signal 500 in FIG. 7. The improved signal-to-noise ratio of the A1 through A3 events and attenuation of the A4 event in the averaged motion signal 500 enables control circuit 206 to reliably detect the signal averaged A1 event 502, A2 event 504 and A3 event 506 for determining one or more ventricular event time intervals for use in setting A1, A2 and A3 detection windows 420, 422, and 424, respectively, setting detection threshold amplitudes for detecting the A1, A2, A3 and/or A4 events, and/or setting atrial refractory period 436 used on a beat-by-beat basis for A4 event detection as shown in FIG. 6.

For example, a ventricular R-wave or pacing pulse to A1 time interval 530, an A1-A3 time interval 534, A1-A2 time interval 536, a ventricular R-wave or pacing pulse to A3 time interval 516, and/or a T-wave to A3 time interval 518 may be determined by control circuit 206 from the averaged motion signal 500 and the cardiac electrical signal 510. The atrial refractory period 436 is started upon delivering a ventricular pacing pulse or sensing an intrinsic R-wave. The atrial refractory period 436 may be set to expire after a predetermined time interval, e.g., 30 to 100 ms, after the A3 time interval 516. For instance, if time interval 516 is 700 ms, the atrial refractory period 436 may be set to expire 750 ms after the ventricular pacing pulse or sensed R-wave that started the atrial refractory period. Instead of using a time interval ending with the A3 event detection, a time interval ending with the A2 event detection may be determined and used in controlling the duration of the atrial refractory period 436. As described above, the A2 event, which occurs during T-wave 514, is an indicator of the end of ventricular mechanical systole and the onset of ventricular mechanical diastole. The A3 event occurs during ventricular mechanical diastole, during the passive ventricular filling phase. As such the timing of the A2 event 504 or the timing of the A3 event 506 relative to another ventricular electrical event (ventricular pacing pulse, R-wave 512, or T-wave 514) may be used for controlling the duration and expiration time of atrial refractory period 436. In other words, the timing of a ventricular mechanical diastolic event, A2 event 504 or A3 event 506, may be determined and used to set the atrial refractory period 436 that is applied on a beat-by-beat basis for detecting A4 events.

The T-wave 514 may be sensed by sensing circuit 206 on a beat-by-beat basis by control circuit 206 or by sensing circuit 204 from cardiac electrical signal 510. The T-wave 514 may be sensed at a maximum peak amplitude of a rectified cardiac electrical signal or a maximum absolute peak amplitude in a non-rectified cardiac signal received by control circuit 206 from sensing circuit 204. Alternatively, T-wave 514 may be sensed by sensing circuit 204 in response to the cardiac electrical signal crossing a T-wave sensing threshold amplitude after the ventricular pacing pulse or R-wave sensed event signal. In some cases, a T-wave sensing window may be applied after the R-wave sensed event signal or a delivered pacing pulse to facilitate T-wave sensing.

The T-wave 514 may be sensed during the atrial refractory period 436. Control circuit 206 may terminate the atrial refractory period 436 at a predetermined time interval after sensing T-wave 514. For instance if the T-wave to A3 time interval 518 is determined to be 150 ms from the averaged motion signal 500, control circuit 206 may terminate the atrial refractory period 436 at 180 ms after sensing the T-wave to promote reliable sensing of the A4 event.

Atrial event detector circuit 240 may be a processor-based circuit that determines the averaged motion sensor signal 500 over multiple cardiac cycles, detects A1, A2 and A3 events 502, 504, and 506 from the averaged motion sensor signal 500, and sets the atrial refractory period 436 based on the timing of at least one ventricular mechanical diastolic event, e.g., the A3 event 506, detected from the average motion sensor signal 500. In other examples, the A2 event is used as a ventricular diastolic mechanical event for marking the approximate timing of the onset of ventricular diastole. The A4 event, e.g., event 408 or 418 (FIG. 6) may be detected on a beat-by-beat basis from the non-averaged motion sensor signal after the atrial refractory period 436 expires. The A3 event 506 may be used to determine an A3 time interval following the A1 event or following a ventricular electrical event, e.g., a sensed R-wave or delivered ventricular pacing pulse. Control circuit 206 may use the A3 time interval determined from the ensemble averaged motion signal for setting a minimum temporary LR interval used for controlling ventricular pacing rate during the non-atrial tracking ventricular pacing mode.

Figure 8:
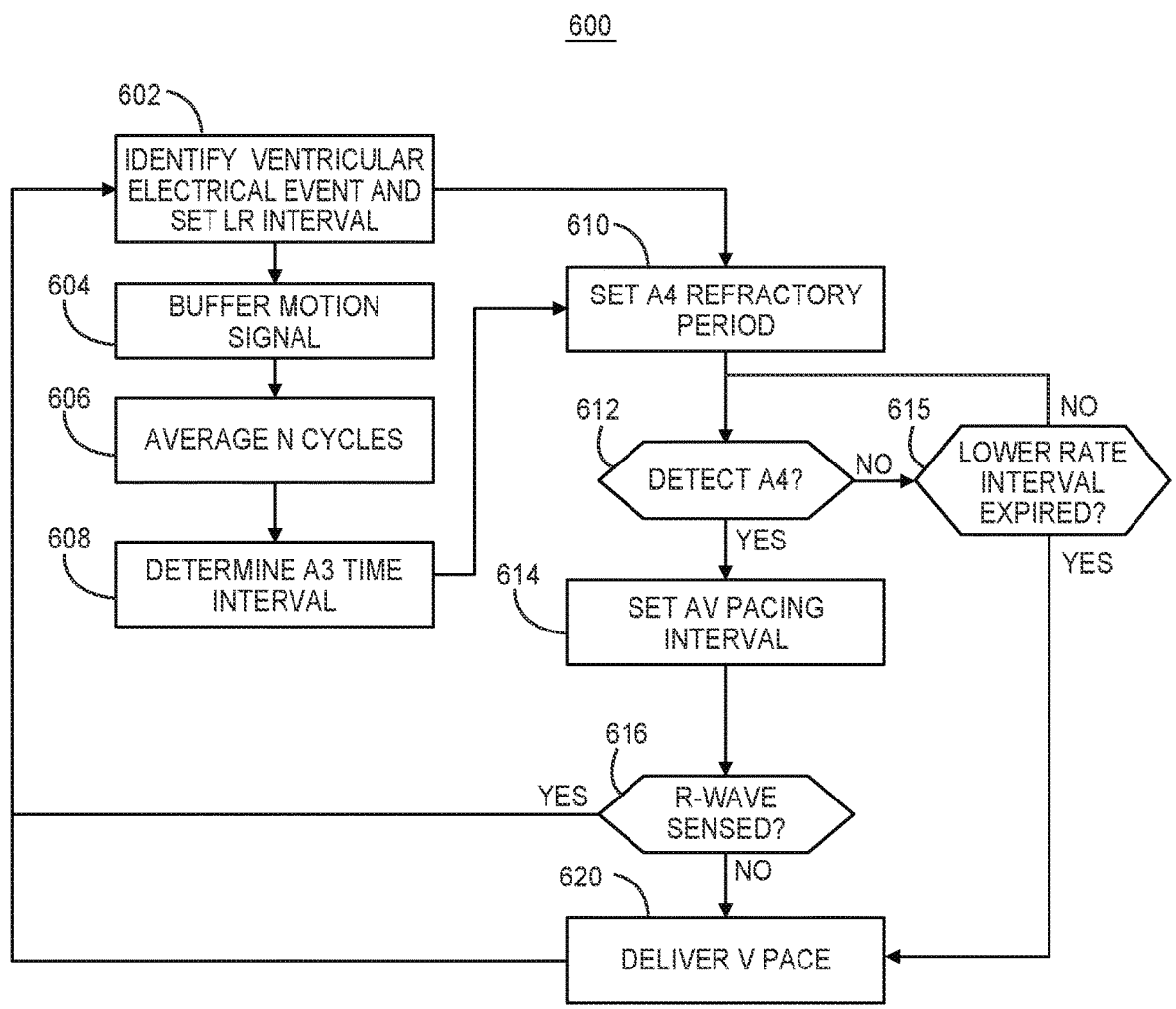
FIG. 8 is a flow chart of a method performed by an intracardiac ventricular pacemaker for detecting atrial events and controlling atrial-synchronized ventricular pacing during an atrial tracking pacing mode according to one example.

FIG. 8 is a flow chart 600 of a method performed by pacemaker 14 for detecting atrial events and controlling atrial-synchronized ventricular pacing during an atrial tracking pacing mode according to one example. At block 602, control circuit 206 identifies a ventricular electrical event, which may be an intrinsic R-wave sensed by sensing circuit 204 or a ventricular pacing pulse delivered by pulse generator 202. A LR pacing interval may be set at block 602 upon identifying the ventricular electrical event, as described in conjunction with FIG. 5, in order to maintain a minimum, base ventricular rate in the absence of A4 event detections.

At block 604, the motion sensor signal is buffered over the cardiac cycle, e.g., until the next ventricular electrical event is identified. At block 606, the buffered motion signal is averaged with buffered motion sensor signals acquired over a predetermined number of cardiac cycles to obtain an averaged motion signal with improved A1, A2 and A3 signal-to-noise ratio and attenuated A4 signal compared to the non-averaged motion sensor signal.

At block 608 the A1-A3 time interval or a ventricular electrical event to A3 time interval is determined from the averaged motion sensor signal by detecting the signal averaged A1, A2 and A3 events as described above in conjunction with FIG. 7. The A3 time interval is used to set the atrial refractory period at block 610 by atrial event detector circuit 240. As described above, the atrial refractory period may be set a predetermined percentage or fixed time interval longer than the A1-A3 time interval or a ventricular electrical event to A3 time interval or set to expire upon expiration of an A3 sensing window that is defined based on relative timing of the A1, A2, and A3 events. In other examples, an A2 time interval is determined at block 608 for use in setting the A4 refractory period. The A2 and A3 events are ventricular mechanical diastolic event markers that may be used for controlling the timing of the expiration of the A4 refractory period to occur near the start or during the ventricular passive filling phase, before the active ventricular filling phase associated with atrial systole.

The atrial refractory period is started at block 610 upon identifying the ventricular electrical event at block 602. In some examples, signal averaging and determination of the A3 time interval (or A2 time interval) for setting the atrial refractory period may occur on a beat-by-beat basis using an averaged motion signal. In other examples, the A3 time interval is determined periodically or in response to a change in the atrial rate, e.g., determined from A4-A4 intervals, or a change between a sensed and paced ventricular rhythm. The most recently updated A3 time interval (or A2 time interval) determined from the averaged motion sensor signal may be used to set the atrial refractory period at block 610. The expiration of the atrial refractory period may be set on the fly during an already started atrial refractory period based on the A3 time interval determined during the current ventricular cycle. In other examples, the A3 time interval determined on a preceding ventricular cycle is used to set the atrial refractory period for the current ventricular cycle so that the atrial refractory period ends during or after an expected time of the A3 event, or in some cases prior to an expected A3 event but after an expected A2 event.

In other examples, the duration of the atrial refractory period may be controlled on a beat-by-beat basis by starting the atrial refractory period upon the identified ventricular event, sensing the T-wave during the atrial refractory period, and terminating the atrial refractory period a predetermined time interval after the sensed T-wave, where the predetermined time interval is based on the T-wave to A3 time interval 518 determined from the averaged motion signal 500 (FIG. 7).

If an A4 event is detected from the non-averaged motion sensor signal at block 612, after the atrial refractory period expires, an AV pacing interval is set at block 614. The A4 event may be detected based on an A4 detection threshold amplitude crossing by the raw motion sensor signal or by the rectified signal. The pace timing circuit 242 sets an AV pacing interval at block 614 in response to the detected A4 signal. If an intrinsic R-wave is not sensed before expiration of the AV pacing interval, as determined at block 616, the scheduled ventricular pacing pulse is delivered at block 620. In some cases, the A4 event may not be detected before a lower rate pacing interval expires at block 615. An atrial-asynchronous ventricular pacing pulse may be delivered at block 620 if the lower rate pacing interval expires before an A4 event is detected to maintain a programmed ventricular base rate, causing the process to return to block 602 where the ventricular pacing pulse is identified as the next ventricular electrical event.

Figure 9:
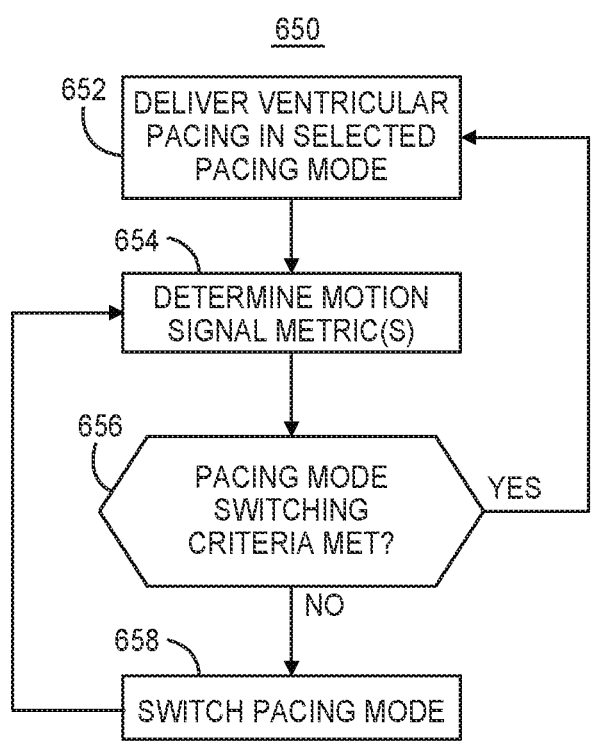
FIG. 9 is a flow chart of a method for controlling the ventricular pacing mode by an intracardiac ventricular pacemaker according to one example.

FIG. 9 is a flow chart 650 of a method for controlling ventricular pacing mode by pacemaker 14 according to one example. Control circuit 206 is configured to control pacemaker 14 to operate in a first pacing mode, either an atrial-tracking pacing mode or a non-atrial tracking pacing mode for controlling ventricular pacing pulses and to determine when to switch to a second pacing mode, the other one of the atrial-tracking pacing mode or the non-atrial tracking pacing mode, based on an analysis of the motion sensor signal.

As shown in FIG. 9, ventricular pacing pulses are delivered according to the selected pacing mode at block 652. For example, the pacemaker 14 may be operating in an atrial-tracking VDD pacing mode during which ventricular pacing pulses are scheduled at an AV pacing interval in response to detecting an A4 event as described above. In the absence of a detected A4 event, a ventricular pacing pulse is delivered at a VDD LR interval when an intrinsic R-wave is not detected before expiration of the LR interval to prevent ventricular asystole. At other times, the pacemaker 14 may be operating in a non-atrial tracking VVIR or VDIR pacing mode during which pacing pulses are scheduled at a ventricular LR pacing interval, which may be a permanent VVIR or VDIR LR interval corresponding to a base pacing rate or a temporary LR interval set based on a patient physical activity metric determined from the motion sensor signal (or other sensor signal correlated to patient metabolic demand).

During operation in the selected ventricular pacing mode, the control circuit 206 is configured to determine one or more motion signal metrics from the motion signal at block 654. The one or more motion signal metrics are compared to first pacing mode switching criteria at block 656. If the first pacing mode switching criteria are met, the control circuit 206 switches from the current, first pacing mode, either an atrial tracking pacing mode or a non-atrial tracking pacing mode, to a second pacing mode. The second pacing mode is the other one of the atrial tracking pacing mode or the non-atrial tracking pacing mode depending on which pacing mode the control circuit 206 is switching from.

During the second pacing mode, the control circuit 206 determines one or more motion signal metrics at block 654, which may be the same motion signal metric(s) or different motion signal metric(s) that were determined during the first pacing mode. Control circuit 206 determines if second pacing mode switching criteria are met by the motion signal metric(s) during the second pacing mode and switches back to the first pacing mode in response to the second pacing mode switching criteria being met.

Among the motion signal metrics that may be determined at block 654 are metrics that are correlated to patient physical activity and/or correlated to loss of reliable A4 event detection. Motion signal metrics correlated to patient physical activity may be a patient activity metric correlated to patient metabolic demand such as an activity count or a sensor indicated pacing rate determined from the patient activity metric. A patient posture may be determined from the motion signal as an indirect indicator of patient activity, e.g., by detecting a non-upright posture as a resting or inactive posture and detecting an upright posture as a non-resting or active posture. Patient posture may also be determined as a motion signal metric that is correlated to loss of reliable A4 event detection since the patient posture may influence the A4 signal strength and reliability of A4 event detection. For example, a particular patient posture, for instance a left side-lying posture or other identified posture, may be determined to confound A4 event detection in an individual patient and be criteria for pacing mode switching.

A motion signal metric that may be determined at block 654 that is correlated to loss of reliable A4 event detection may be a count of ventricular cycles that occur without a detected A4 event. Another motion signal metric that may be correlated to a loss of reliable A4 event detection may be the A3-A4 time interval. Shortening of the A3-A4 time interval, e.g., interval 445 in FIG. 6, or another ventricular event to A4 time interval, may indicate an increasing atrial rate that may lead to fusion of the A3 and A4 events and/or be associated with increased patient physical activity, both of which may confound A4 event detections.

A motion signal metric that may be determined at block 654 that is correlated to both patient physical activity and loss of reliable A4 event detection may be determined by processing motion signal sample points acquired over a predetermined time segment of the motion signal. For example, the average amplitude of all sample points during the predetermined time segment, a summation of the sample point amplitudes during predetermined time segment, the mean frequency during the time segment, mean slope, or other metric of the motion signal energy or entropy during the entirety of the predetermined time segment may indicate an increase in patient physical, non-cardiac motion, signal noise and/or a potential decrease in the reliability of A4 event detection due to increased motion signal peaks present in the motion signal. The time segment for determining the motion signal metric may be one cardiac cycle or portion thereof or may be independent of cardiac cycle timing, e.g., any 500 ms, 1 second, 2 second or other predetermined time segment or multiple predetermined time segments of the motion sensor signal.

Accordingly, the one or more motion signal metrics determined at block 654 may include direct or indirect metrics of non-cardiac, patient physical motion and/or A4 event detection reliability. The motion signal metrics determined from the motion sensor signal included in pacemaker 14 may include metrics of patient physical activity; patient body posture; A4 event detection counts; cardiac mechanical event (A1, A2, A3, and/or A4) time intervals, amplitudes and/or other features; and motion signal metrics determined by processing the motion signal sample points over a predetermined time segment to obtain a metric correlated to the motion signal energy and/or entropy over the entirety of the time segment. Methods for controlling pacing mode switching between an atrial tracking ventricular pacing mode and a non-atrial tracking ventricular pacing mode are disclosed in the above-incorporated U.S. patent application Ser. No. 15/366,993 (Sheldon, et al.).

Figure 10:
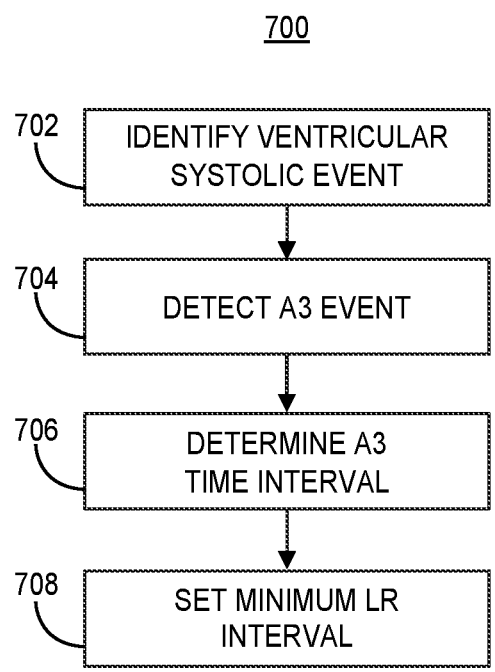
FIG. 10 is a flow chart of a method performed by an intracardiac ventricular pacemaker for establishing a minimum ventricular lower rate interval during a non-tracking atrial pacing mode according to one example.

FIG. 10 is a flow chart 700 of a method performed by RV pacemaker 14 for establishing a minimum ventricular LR interval according to one example. At block 702, RV pacemaker 14 identifies a ventricular systolic event. The ventricular systolic event may be a ventricular pacing pulse delivered by pulse generator 202, an intrinsic R-wave sensed by sensing circuit 204, or a sensed A1 event detected from the motion sensor signal by control circuit 206.

At block 704, control circuit 206 detects the A3 event from the motion sensor signal. The A3 event is detected from the motion signal produced by motion sensor 212 enclosed within the housing 150 of pacemaker 14, which is implanted within the ventricular chamber of a beating heart. As described above, the housing 150 is configured to be implanted wholly within a ventricular heart chamber, e.g., by having a size and shape that is deliverable by a transvenous catheter. Housing 150 may have a generally cylindrical shape with an outer diameter that is 10 mm or less, 8 mm or less, 6 mm or less, or approximately 20 French to accommodate implantation wholly within the heart. The A3 event detected from the intra-ventricular motion signal marks the time of passive ventricular filling during which ventricular pacing pulse delivery is undesirable. If a ventricular pacing pulse is delivered during the passive filling phase, incomplete filling of the ventricle may lead to deleterious hemodynamic consequences. After detecting the A3 event, an A3 time interval is determined at block 706 as the time interval from the identified ventricular systolic event to the detected A3 event. The A3 time interval may be determined for multiple cardiac cycles to determine a median, mean or other statistical measure of centeredness, maximum or range of the A3 time interval. In some examples, the motion sensor signal is averaged over multiple cardiac cycles and the A3 interval is determined from the averaged motion sensor signal, which may have improved signal to noise ratio of ventricular A1, A2 and A3 events compared to the motion sensor signal over a signal cardiac cycle. The A3 time interval determined at block 706 may be the updated A1-A3 time interval trend determined at block 708 in FIG. 5 that is used to set the A4 refractory period during the atrial tracking ventricular pacing mode. The A3 time interval determined at block 706 may alternatively be determined as the A3 time interval determined from the ensemble averaged motion signal at block 608 of FIG. 8 during the atrial tracking ventricular pacing mode. The A3 time interval may be determined during a resting state of the patient, e.g., when the SIR indicates a pacing rate that is not greater than the base pacing rate, or during non-strenuous activity, e.g., when the SIR is not greater than an activities of daily living (ADL) rate.

Pacemaker 14 may be operating in the atrial tracking ventricular pacing mode at the time that the A3 time interval is determined since conditions for pacing mode switching to the non-atrial tracking ventricular pacing mode may not be satisfied when the patient is resting or engaged in non-strenuous activity. In some cases, however, the A3 time interval may be determined during the non-atrial tracking ventricular pacing mode if pacing mode switching criteria have been met. For instance, if a particular patient posture has been detected that is correlated to unreliable A4 event sensing, pacemaker 14 may be operating in a VVIR pacing mode when the process of FIG. 10 is performed. The A3 time interval, however, may be determined during the non-atrial tracking ventricular pacing mode when the pacing rate or sensed ventricular rate is below a predetermined threshold or up to the ADL rate, for example.

If pacemaker 14 is delivering ventricular pacing pulses during the determination of the A3 time interval, the Vpace-A3 time interval may be determined at block 706. This A3 time interval is an estimate of the time from a delivered ventricular pacing pulse until the ventricular passive filling phase and provides a basis for a minimum pacing interval during rate responsive, non-atrial tracking ventricular pacing. If ventricular pacing is not occurring during A3 time interval determination, an R-A3 or an A1-A3 time interval may be determined at block 706. The R-A3 time interval represents the time interval from the intrinsic R-wave to passive filling during a non-paced ventricular rhythm. The A1-A3 time interval represents the time interval from the A1 event to the A3 event of the motion sensor signal. The R-A3 time interval may be different than the Vpace A3 time interval since the time from the ventricular pacing pulse until the electrical depolarization of the myocardium is not included in the R-A3 time interval and the conduction time through the ventricles may be different during an intrinsic beat than during a paced beat. Likewise, the A1-A3 time interval is expected to be different than the Vpace-A3 time interval since the time from the ventricular pacing pulse until the mechanical systole corresponding to the A1 event is not included in the A1-A3 time interval. If ventricular pacing is not occurring during A3 time interval determination at block 706 such that the Vpace-A3 time interval is not available for measurement, the R-A3 or A1-A3 time interval may be determined and adjusted to better approximate a Vpace-A3 time interval that takes into account a delay from the time of a pacing pulse delivery until electrical depolarization or mechanical activation.

At block 708, control circuit 206 establishes a minimum LR interval for limiting the maximum pacing rate during a rate responsive, non-atrial tracking ventricular pacing mode. The minimum LR interval is based on the A3 time interval determined at block 706. In one example, the minimum LR interval may be set as a percentage of the A3 time interval, e.g., 110% to 120% of the A3 time interval or a fixed time interval adjustment may be applied to the A3 time interval, e.g., 10 to 50 ms may be added to the A3 time interval. The minimum LR interval sets a rate responsive pacing rate maximum rate limit for promoting completion of at least the passive ventricular filling phase prior to pacing pulse delivery during increased physical activity of the patient.

In some examples, the A3 time interval may be determined for multiple heart rates at block 706 to generate a table or function of the A3 time interval dependent on heart rate. Since the A3 time interval may change with heart rate, A3 time intervals may be binned for several cardiac cycles after the ventricular rate (paced or intrinsic) has been stable for a predetermined number of cycles. The resting A3 time interval may be used to set the minimum LR interval at block 708. In other examples, the A3 time interval for higher heart rates, at which A4 event detection may become compromised, may be determined or extrapolated from binned A3 time intervals determined for multiple heart rates and used to set the minimum LR interval at block 708. The A3 time interval may be determined for multiple heart rates during an atrial-tracking pacing mode when the A3 and A4 events are being reliably detected. A corrected A3 time interval may be extrapolated for a heart rate greater than the plurality of heart rates and used to establish the minimum pacing rate interval based on the corrected A3 time interval.

Figure 11:
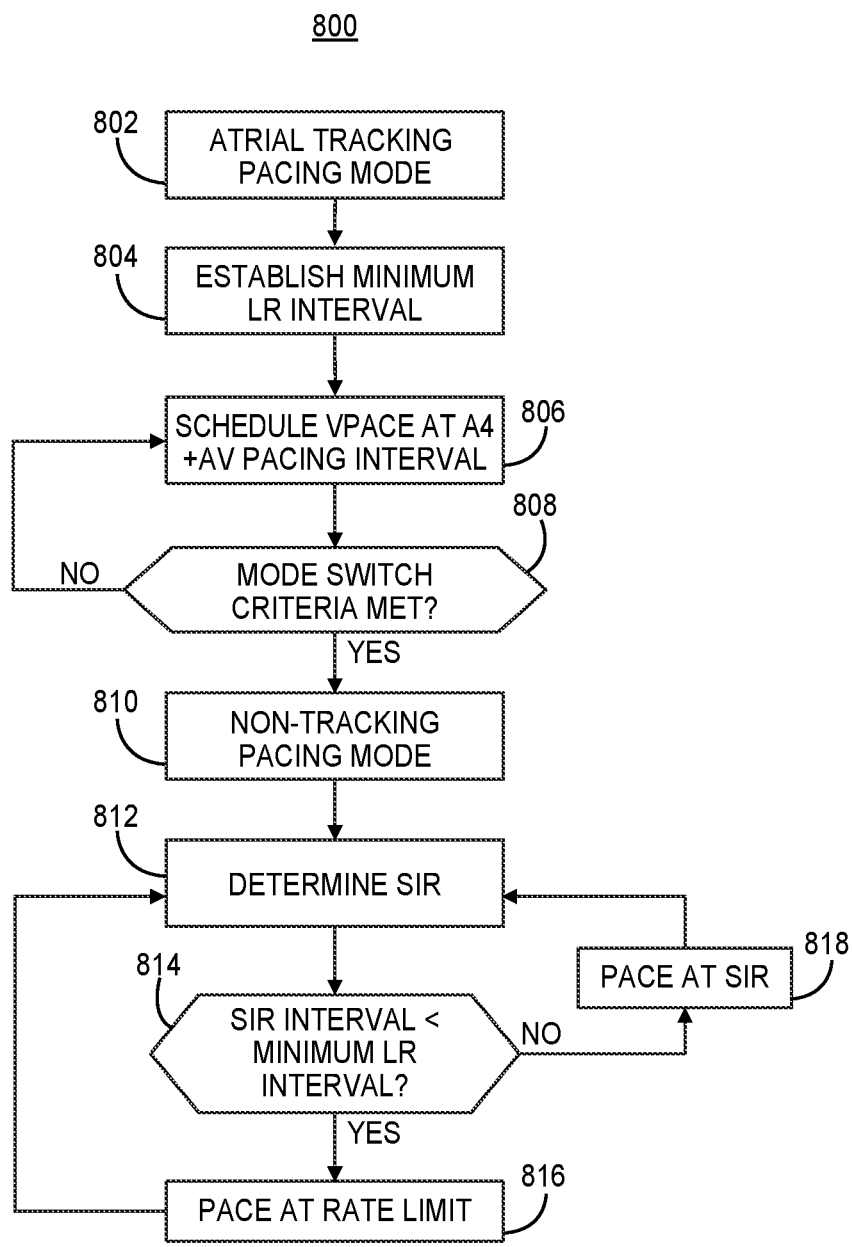
FIG. 11 is a flow chart of one method performed by an intracardiac ventricular pacemaker for controlling ventricular pacing according to one example.

FIG. 11 is a flow chart 800 of one method performed by RV pacemaker 14 for controlling ventricular pacing according to one example. At block 802, pacemaker 14 is initially operating in the atrial tracking ventricular pacing mode, e.g. as described above in conjunction with FIG. 8. During the atrial tracking pacing mode, pacemaker 14 establishes a minimum LR interval at block 804. The minimum LR interval may be established based on an A3 time interval using any of the techniques described above. The minimum LR interval defines the shortest ventricular pacing interval corresponding to a maximum pacing rate that can be delivered during a rate responsive, non-atrial tracking ventricular pacing mode. The minimum LR interval may be established while the patient is at rest or engaged in sub-maximal or relatively low level of physical activity (e.g., ADL) and may be based on a Vpace-A3, R-A3, or A1-A3 time interval as described above. In this way, the minimum LR interval may be established at a time that the A3 and A4 events are reliably detectable, before fusion of A3 and A4 events which may occur during higher heart rates, e.g., associated with increased patient activity.

During the atrial tracking pacing mode, control circuit 206 detects A4 events at block 806 and sets an AV pacing interval in response to detecting an A4 event for scheduling atrial-synchronized ventricular pacing pulses. If an intrinsic R-wave is not sensed, control circuit 206 controls pulse generator 202 to deliver a ventricular pacing pulse at the expiration of the AV interval. In some examples, control circuit 206 may set an A4 refractory period in response to a ventricular event, sensed or paced, during which A4 event detection is inhibited or ignored. The A4 refractory period may be based on a previously measured A3 time interval, e.g., to a percentage longer than or a fixed interval longer than the A1-A3 time interval. During the atrial refractory period, any motion sensor events that are detected may be ignored for the purposes of triggering a ventricular pacing pulse and starting an AV pacing interval. Ventricular mechanical events A1 through A3 may be detected during the atrial refractory period to update the A4 refractory period and update the A3 time interval.

At block 808, control circuit 206 determines if pacing mode switching criteria are met. Control circuit 206 may determine one or more motion signal metrics at block 808 and compare the metric(s) to pacing mode switching criteria. Among the motion signal metrics that may be determined at block 808 are metrics that are correlated to patient physical activity and/or correlated to loss of reliable A4 event detection. Motion signal metrics correlated to patient physical activity may be a patient activity metric correlated to patient metabolic demand such as an activity count or a SIR determined from the patient activity metric. A patient posture may be determined from the motion signal as an indirect indicator of patient activity, e.g., by detecting a non-upright posture as a resting or inactive posture and detecting an upright posture as a non-resting or active posture. Patient posture may also be determined as a motion signal metric that is correlated to loss of reliable A4 event detection since the patient posture may influence the A4 signal strength and reliability of A4 event detection. For example, a particular patient posture may be determined to confound A4 event detection in an individual patient and be criteria for pacing mode switching.

A motion signal metric that may be determined at block 808 that is correlated to loss of reliable A4 event detection may be patient activity, patient posture, or a count of ventricular cycles that occur without a detected A4 event. Another motion signal metric that may be correlated to a loss of reliable A4 event detection may be the A3-A4 time interval. Shortening of the time interval between a detected A3 and a detected A4 event, or another ventricular event to A4 time interval, may indicate an increasing atrial rate that may lead to fusion of the A3 and A4 events and/or be associated with increased patient physical activity, both of which may confound A4 event detection. Techniques generally disclosed in the above-incorporated '993 application for controlling ventricular pacing mode switching from an atrial tracking pacing mode to a non-atrial tracking pacing mode based on motion sensor signal metric(s) may be used at block 808. The mode switching criteria may be defined to promote switching to non-atrial tracking ventricular pacing when A4 events are or at risk of being under-detected and ventricular rate support is needed. The mode switching criteria may be defined to preferentially provide atrial synchronized ventricular pacing when A4 events are being detected or when A4 events are not being detected but ventricular pacing at the programmed lower rate is adequate for supporting the patient's physical activity level, e.g., a resting state.

If mode switching criteria are met at block 808, control circuit 206 switches to the non-atrial tracking ventricular pacing mode at block 810. The non-atrial tracking pacing mode may be a rate responsive mode to provide ventricular rate support during periods of increased patient activity. As such, control circuit 206 may determine a SIR from the motion sensor signal at block 812. Methods for determining a SIR are generally described in the above-incorporated references. Techniques for limiting a maximum rate response pacing rate using the A3 time interval as disclosed herein are not limited to a particular method for determining the SIR. Control circuit 206 determines the ventricular pacing interval corresponding to the SIR at block 814 and compares this SIR interval to the minimum LR interval previously established during the atrial tracking pacing mode (at block 804). If the SIR interval is equal to or greater than the minimum LR interval, control circuit 206 controls pulse generator 204 to schedule ventricular pacing pulses at a temporary LR interval set equal to the SIR interval at block 818.

If the SIR interval is less than minimum LR interval, pacing at the SIR may cause ventricular pacing pulses to be delivered during passive filling of the ventricle. In response to the SIR interval being less than the minimum LR interval at block 814, control circuit 206 controls the pulse generator 202 to deliver ventricular pacing pulses a rate response limit defined by the minimum LR interval. For example, the A3 time interval determined during the atrial tracking pacing mode may be 400 ms. A minimum LR interval may be set to 20 ms greater than the A3 time interval, 420 ms in this example. The minimum LR interval of 420 ms corresponds to a rate response limit of 136 pacing pulses per minute. If the SIR determined at block 412 based on a patient activity metric derived from the motion sensor signal is greater than 136 pulses per minute, control circuit 206 controls pulse generator 202 to schedule pacing pulses at the maximum rate response limit of 136 pulses per minute at block 816 (at the minimum LR interval of 420 ms). As long as the SIR interval is equal to or longer than the minimum LR interval, control circuit 206 schedules ventricular pacing pulses at the SIR interval and controls pulse generator 202 to deliver pacing pulses at the SIR at block 818.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device, comprising:
 a pulse generator configured to deliver cardiac pacing pulses;
 a motion sensor configured to produce a motion signal;
 a sensing circuit configured to receive a cardiac electrical signal and sense R-waves from the cardiac electrical signal;
 a control circuit coupled to the motion sensor, the sensing circuit, and the pulse generator, the control circuit configured to:
  identify a ventricular systolic event as one of a ventricular pacing pulse delivered by the pulse generator or an R-wave sensed by the sensing circuit;
  detect a ventricular passive filling event signal from the motion signal;
  determine a time interval from the ventricular systolic event to the ventricular passive filling event; and
  establish a minimum rate response pacing interval based on the time interval from the ventricular systolic event to the ventricular passive filling event, the minimum rate response pacing interval corresponding to a maximum pacing rate; and
 a memory in communication with the control circuit and configured to store the minimum rate response pacing interval; and
 the pulse generator is configured to deliver one or more pacing pulses at the maximum pacing rate.

2. The medical device of claim 1, wherein:
 the control circuit is further configured to:
  determine a sensor indicated pacing rate interval; and
  determine that the sensor indicated pacing rate interval is less than the minimum pacing interval;
 the pulse generator is configured to deliver a pacing pulse at the minimum pacing interval corresponding to the maximum pacing rate in response to the sensor indicated pacing rate interval being less than the minimum pacing interval.

3. The medical device of claim 2, wherein the control circuit is further configured to determine the sensor indicated pacing rate interval based on the motion signal.

4. The medical device of claim 3, wherein:
 the control circuit is further configured to switch from an atrial tracking pacing mode for controlling the pulse generator to deliver atrial synchronized pacing pulses to a non-atrial tracking pacing mode for controlling the pulse generator to deliver atrial asynchronous pacing pulses; and
 the pulse generator is further configured to deliver ventricular pacing pulses in the non-atrial tracking pacing mode by delivering a pacing pulse at the sensor indicated pacing rate interval when the sensor indicated pacing rate interval is greater than the minimum pacing interval.

5. The medical device of claim 2, wherein the control circuit is further configured to:
 determine that pacing mode switching criteria are satisfied; and
 determine the sensor indicated rate in response to the pacing mode switching criteria being satisfied.

6. The medical device of claim 1, wherein:
 the control circuit is further configured to:
  detect an atrial systolic event from the motion signal,
  set an atrioventricular pacing interval in response to detecting the atrial systolic event, and the pulse generator is further configured to deliver at least one pacing pulse in an atrial tracking pacing mode by delivering the at least one pacing pulse upon expiration of the atrioventricular pacing interval; and the control circuit is configured to determine the time interval from the ventricular systolic event to the ventricular passive filling event during the atrial tracking pacing mode.

7. The medical device of claim 1, wherein the control circuit is configured to:
   detect a resting stable heart rate; and
   determine the time interval from the ventricular systolic event to the ventricular passive filling event during the resting stable heart rate.

8. The medical device of claim 1, wherein the control circuit is configured to:
   determine the time interval from the ventricular systolic event to the ventricular passive filling event for each of a plurality of heart rates;
   extrapolate a corrected time interval from the ventricular systolic event to the ventricular passive filling event for a heart rate greater than the plurality of heart rates; and
   establish the minimum pacing interval based on the corrected time interval.

9. The medical device of claim 1, wherein the control circuit is further configured to determine the time interval from the ventricular systolic event to the ventricular passive filling event from the motion signal acquired over a plurality of cardiac cycles.

10. A non-transitory, computer-readable medium storing a set of instructions, which, when executed by a control circuit of a medical device having a pulse generator for delivering cardiac pacing pulses and a motion sensor, cause the medical device to:
    produce a motion signal by the motion sensor;
    receive a cardiac electrical signal;
    sense R-waves from the cardiac electrical signal;
    identify a ventricular systolic event as one of a ventricular pacing pulse delivered by the pulse generator or a sensed R-wave;
    detect a ventricular passive filling event signal from the motion signal;
    determine a time interval from the ventricular systolic event to the ventricular passive filling event;
    establish a minimum rate response pacing interval based on the time interval from the ventricular systolic event to the ventricular passive filling event, the minimum rate response pacing interval corresponding to a maximum pacing rate;
    store the minimum rate response pacing interval; and
    deliver one or more pacing pulses at the maximum pacing rate.

11. The non-transitory, computer-readable medium of claim 10, further comprising instructions that cause the medical device to:
    determine a sensor indicated pacing rate interval;
    determine that the sensor indicated pacing rate interval is less than the minimum pacing interval; and
    deliver a pacing pulse at the minimum pacing interval corresponding to the maximum pacing rate in response to the sensor indicated pacing rate interval being less than the minimum pacing interval.

12. The non-transitory, computer-readable medium of claim 11, further comprising instructions that cause the medical device to determine the sensor indicated pacing rate interval based on the motion signal.

13. The non-transitory, computer-readable medium of claim 12, further comprising instructions that cause the medical device to:
    switch from an atrial tracking pacing mode for controlling the pulse generator to deliver atrial synchronized pacing pulses to a non-atrial tracking pacing mode for controlling the pulse generator to deliver atrial asynchronous pacing pulses; and
    deliver ventricular pacing pulses by the pulse generator in the non-atrial tracking pacing mode by delivering a pacing pulse at the sensor indicated pacing rate interval when the sensor indicated pacing rate interval is greater than the minimum pacing interval.

14. The non-transitory, computer-readable medium of claim 11, further comprising instructions that cause the medical device to:
    determine that pacing mode switching criteria are satisfied; and
    determine the sensor indicated rate in response to the pacing mode switching criteria being satisfied.

15. The non-transitory, computer-readable medium of claim 10, further comprising instructions that cause the medical device to:
    detect an atrial systolic event from the motion signal,
    set an atrioventricular pacing interval in response to detecting the atrial systolic event,
    deliver by the pulse generator at least one pacing pulse in an atrial tracking pacing mode by delivering the at least one pacing pulse upon expiration of the atrioventricular pacing interval; and
    determine the time interval from the ventricular systolic event to the ventricular passive filling event during the atrial tracking pacing mode.

16. The non-transitory, computer-readable medium of claim 10, further comprising instructions that cause the medical device to:
    detect a resting stable heart rate; and
    determine the time interval from the ventricular systolic event to the ventricular passive filling event during the resting stable heart rate.

17. The non-transitory, computer-readable medium of claim 10, further comprising instructions that cause the medical device to:
    determine the time interval from the ventricular systolic event to the ventricular passive filling event for each of a plurality of heart rates;
    extrapolate a corrected time interval from the ventricular systolic event to the ventricular passive filling event for a heart rate greater than the plurality of heart rates; and
    establish the minimum pacing interval based on the corrected time interval.

18. The non-transitory, computer-readable medium of claim 10, further comprising instructions that cause the medical device to determine the time interval from the ventricular systolic event to the ventricular passive filling event from the motion signal acquired over a plurality of cardiac cycles.

19. A method, comprising:
    producing a motion signal by a motion sensor;
    sensing R-waves from a cardiac electrical signal;
    identifying a ventricular systolic event as one of a ventricular pacing pulse or a sensed R-wave;
    detecting a ventricular passive filling event signal from the motion signal;
    determining a time interval from the ventricular systolic event to the ventricular passive filling event;

establishing a minimum rate response pacing interval based on the time interval from the ventricular systolic event to the ventricular passive filling event, the minimum rate response pacing interval corresponding to a maximum pacing rate; and storing the minimum rate response pacing interval; and delivering by a pulse generator that is responsive to the stored minimum rate response pacing interval one or more pacing pulses at the maximum pacing rate.

* * * * *